(12) United States Patent
Vasefi et al.

(10) Patent No.: US 12,023,415 B2
(45) Date of Patent: Jul. 2, 2024

(54) INSPECTION AND SANITATION DEVICE AND METHOD

(71) Applicant: SafetySpect Inc., Sherman Oaks, CA (US)

(72) Inventors: Fartash Vasefi, Sherman Oaks, CA (US); Kenneth Edward Barton, Palm City, FL (US); Nicholas Bennett MacKinnon, Salt Spring Island (CA); David Carroll, Arlington, VA (US); Sava Marinkovich, Chicago, IL (US)

(73) Assignee: SafetySpect Inc, Grand Forks, ND (US)

(*) Notice: Subject to any disclaimer, the term of this patent is extended or adjusted under 35 U.S.C. 154(b) by 196 days.

(21) Appl. No.: 17/161,567

(22) Filed: Jan. 28, 2021

(65) Prior Publication Data

US 2021/0228757 A1    Jul. 29, 2021

Related U.S. Application Data

(60) Provisional application No. 63/012,804, filed on Apr. 20, 2020, provisional application No. 62/967,514, filed on Jan. 29, 2020.

(51) Int. Cl.
| | |
|---|---|
| A61L 2/28 | (2006.01) |
| A61L 2/08 | (2006.01) |
| A61L 2/10 | (2006.01) |
| G01N 21/64 | (2006.01) |
| G06T 11/00 | (2006.01) |
| H04N 23/45 | (2023.01) |
| H04N 23/56 | (2023.01) |

(52) U.S. Cl.
CPC ............... *A61L 2/28* (2013.01); *A61L 2/084* (2013.01); *A61L 2/10* (2013.01); *G01N 21/6456* (2013.01); *G01N 21/6486* (2013.01); *G06T 11/001* (2013.01); *H04N 23/45* (2023.01); *H04N 23/56* (2023.01); *A61L 2202/11* (2013.01); *A61L 2202/14* (2013.01)

(58) Field of Classification Search
CPC ... A61L 2/28; A61L 2/084; A61L 2/10; A61L 2202/11; A61L 2202/14; G01N 21/6456; G01N 21/6486; G06T 11/001; H04N 5/2256; H04N 5/2258
See application file for complete search history.

(56) References Cited

U.S. PATENT DOCUMENTS 10,426,852 B2 * 10/2019 Dobrinsky ............... A61L 9/00

OTHER PUBLICATIONS

Jun et al, "Microbial biofilm detection on food court contact surfaces by macro-scale fluorescence imaging" Journal of Food Engineeing 88 (2010), pp. 314-322. (Year: 2010).*

* cited by examiner

*Primary Examiner* — David P Porta
*Assistant Examiner* — Fani Polyzos Boosalis

(57) ABSTRACT

A device is disclosed. The device contains a first light source configured to excite fluorescence emission of a first contaminant on a surface, and a first optical sensor configured to capture one or more images of the fluorescence emission of the first contaminant.

16 Claims, 33 Drawing Sheets

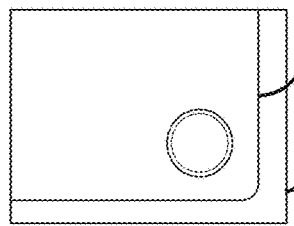
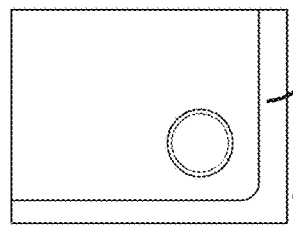
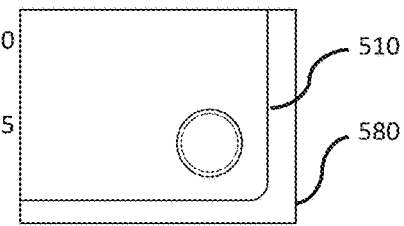
Figure 19h Figure 19i Figure 19j
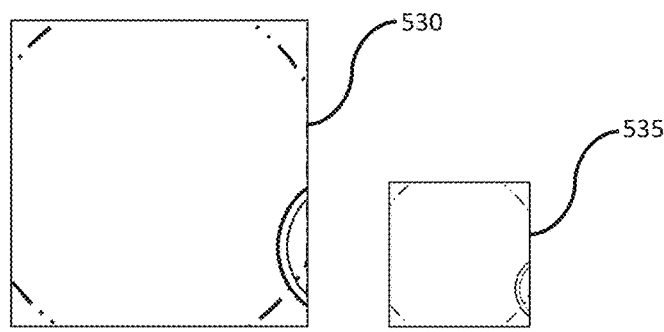
Figure 19k Figure 19l
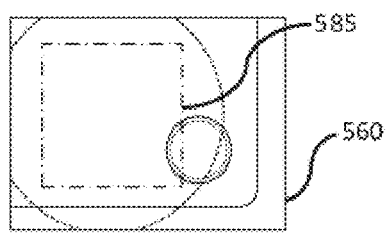
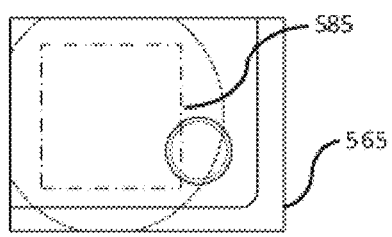
Figure 19m Figure 19n

INSPECTION AND SANITATION DEVICE AND METHOD

CROSS REFERENCE TO RELATED APPLICATIONS

This application claims the benefit of U.S. Provisional Application No. 62/967,514, filed on Jan. 29, 2020, which is incorporated herein by reference in its entirety. This application claims the benefit of U.S. Provisional Application No. 63/012,804, filed on Apr. 20, 2020, which is incorporated herein by reference in its entirety.

FIELD

The present invention relates to a device. More particularly, the present invention relates to an inspection device, and an inspection device configured to sanitize.

BACKGROUND

In many industries such as the food preparation industry, transportation industry, hospitality industry and care home industry, surfaces that may be touched frequently must be cleaned to remove potentially harmful pathogens such as bacteria, viruses, mold, or fungi which may be contained in organic residues or human fluids deposited on such surfaces. Cleaning of such surfaces is essential to maintain public health and must be performed prior to resuming use of the surfaces.

For example, in the food preparation industry, a food preparation station must be sufficiently cleaned before transitioning to prepare a new food product so as to avoid cross contamination between the first food product ingredients or the first preparer, and the second food product ingredients or second preparer. To ensure the effectiveness of a cleaning process such surfaces must be verified to have been effectively cleaned prior to releasing the surface for use on a new process or product. For example, food safety regulations require inspection of preparation surfaces prior to returning those surfaces to use.

In another example, in the transportation industry, a passenger spending an extended time in a particular area such as a seat or restroom, may extensively contact certain surfaces such as handles or tray tables. If the passenger has a contagious illness that can be spread by touch, coughing or spilled food, these surfaces may be contaminated.

Inspection for contamination is typically performed through visual inspection by human operators. However, visual inspection is prone to interpersonal variations such as eyesight and age of inspector, the training level of the inspector, and errors due to environmental differences such as lighting conditions, viewing angle and distance, and other possible issues affecting perception. Furthermore, visual inspection is not a quantitative method. Following inspection, the actual level of residue on the surface is not known at the time of inspection and the inspection process cannot be validated as to its accuracy, precision, or limits of cleanliness. The only documentation that the visual inspection was actually performed is the signature of the operator. While a visual "threshold" limit may be assumed based on academic publications, since there is no quantitative measure or objective record, existing assessment methods are qualitative, resulting in a pass or fail assessment. They are also subjective rather than quantitative and objective, or repeatable and consistent.

When an inspector does detect the presence of contamination it can be removed by cleaning with an appropriate method but until it is no longer visually apparent, but the problem of whether it is actually clean of invisible contaminants still exists.

One other method of inspection for contamination is swab-based testing such as the use of ATP testing swabs. These swabs then need to be analyzed by a machine, that is commonly in an off-site or onsite laboratory, resulting in delays in assessment and potentially costly delays in cleaning and disinfection.

Existing methods of disinfection include treatment with chemicals by hand, chemical fogging and disinfection with ionizing radiation or nonionizing radiation. Some of these methods are dangerous to operators and are slow to apply unless it is targeted at a specific site.

There needs to be a device and/or method of detecting contaminants on a surface/object. There further needs to be a device and/or method for disinfecting contaminated surface/object.

SUMMARY OF THE INVENTION

Generally speaking, pursuant to the various embodiments, according to one aspect, a device is presently disclosed. The device comprises a first light source configured to excite fluorescence emission of a first contaminant on a surface; a first optical sensor configured to capture one or more images of the fluorescence emission of the first contaminant; and a display configured to depict the surface and a computer generated image representing the contaminant, wherein the computer generated image covers at least a portion of the surface shown on the display. According to a second aspect, a device is presently disclosed. The device comprises a first light source configured to excite fluorescence emission of a first contaminant on a surface; and a first optical sensor configured to capture one or more images of the fluorescence emission of the first contaminant. According to a third aspect, a device is presently disclosed. The device comprises a first light source configured to excite fluorescence emission of a first contaminant on a surface; a first optical sensor configured to capture one or more images of the fluorescence emission of the first contaminant; a second light source configured to excite fluorescence emission of the first contaminant on the surface; a second optical sensor configured to capture one or more images of the fluorescence emission of the first contaminant. According to a fourth aspect, a device is presently disclosed. The device comprises a first light source configured to excite fluorescence emission of a first contaminant on a surface; and a first optical sensor configured to capture one or more images of the fluorescence emission of the first contaminant; wherein the first light source comprises illumination of suitable wavelengths and power to disinfect and/or deactivate the first contaminant. According to a fifth aspect, a device is presently disclosed. The device comprises a first light source configured to excite fluorescence emission of a first contaminant on a surface; a first optical sensor configured to capture one or more images of the fluorescence emission of the first contaminant; a second light source configured to excite fluorescence emission of the first contaminant on the surface; a second optical sensor configured to capture one or more images of the fluorescence emission of the first contaminant; wherein the first light source comprises illumination of suitable wavelengths and power to disinfect and/or deactivate the first contaminant.

Figure 1:
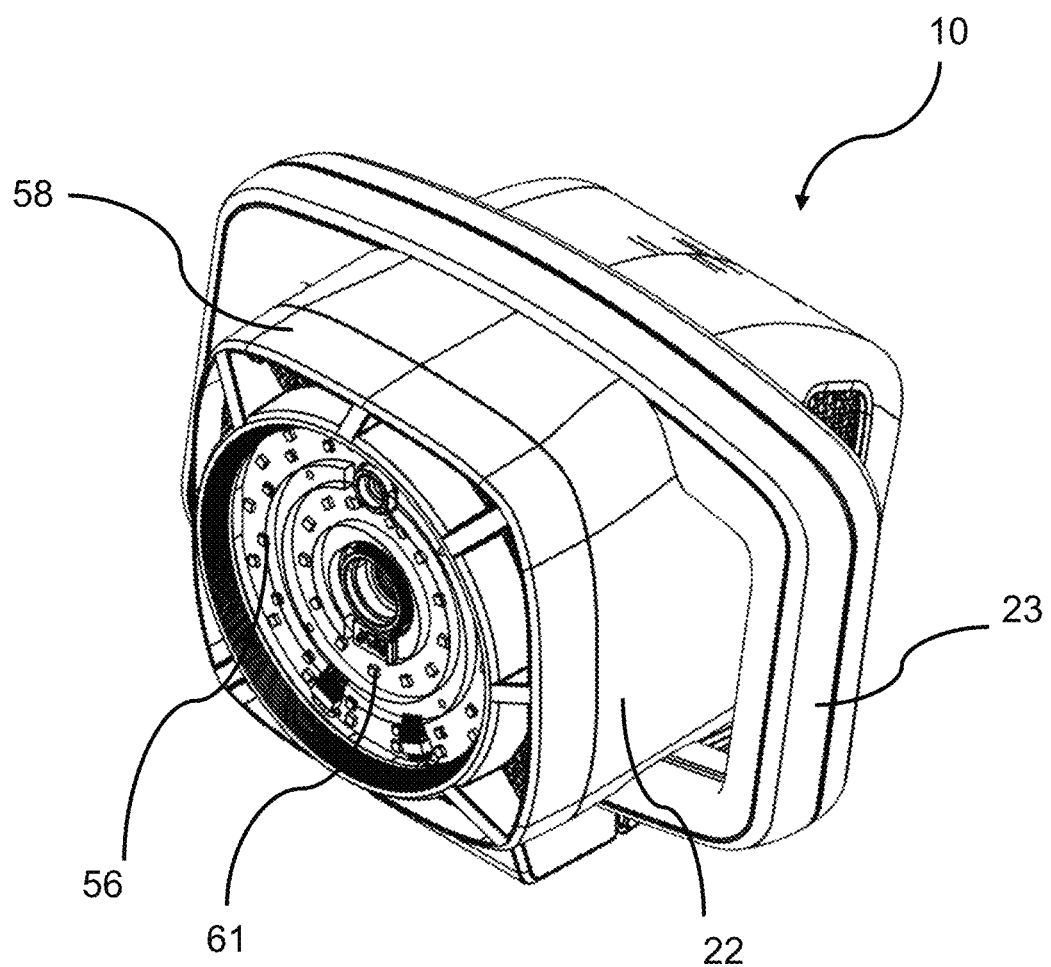
FIG. 1 depicts a front perspective view of a device according to some embodiments presently disclosed.
Figure 2:
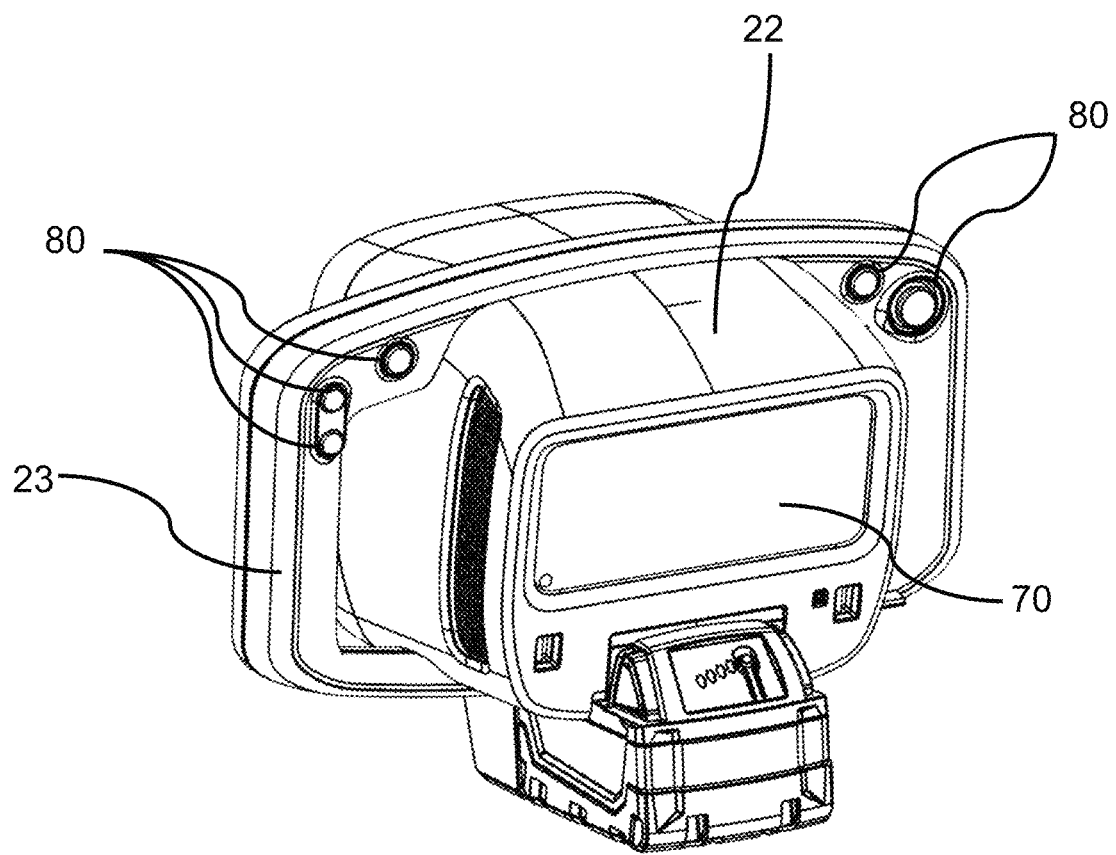
FIG. 2 depicts a rear perspective view of the device in FIG. 1.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Generally speaking, pursuant to the various embodiments, according to one aspect, a device is presently disclosed. The device comprises a first light source configured to excite fluorescence emission of a first contaminant on a surface; a first optical sensor configured to capture one or more images of the fluorescence emission of the first contaminant; and a display configured to depict the surface and a computer generated image representing the contaminant, wherein the computer generated image covers at least a portion of the surface shown on the display. According to a second aspect, a device is presently disclosed. The device comprises a first light source configured to excite fluorescence emission of a first contaminant on a surface; and a first optical sensor configured to capture one or more images of the fluorescence emission of the first contaminant. According to a third aspect, a device is presently disclosed. The device comprises a first light source configured to excite fluorescence emission of a first contaminant on a surface; a first optical sensor configured to capture one or more images of the fluorescence emission of the first contaminant; a second light source configured to excite fluorescence emission of the first contaminant on the surface; a second optical sensor configured to capture one or more images of the fluorescence emission of the first contaminant. According to a fourth aspect, a device is presently disclosed. The device comprises a first light source configured to excite fluorescence emission of a first contaminant on a surface; and a first optical sensor configured to capture one or more images of the fluorescence emission of the first contaminant; wherein the first light source comprises illumination of suitable wavelengths and power to disinfect the first contaminant. According to a fifth aspect, a device is presently disclosed. The device comprises a first light source configured to excite fluorescence emission of a first contaminant on a surface; a first optical sensor configured to capture one or more images of the fluorescence emission of the first contaminant; a second light source configured to excite fluorescence emission of the first contaminant on the surface; a second optical sensor configured to capture one or more images of the fluorescence emission of the first contaminant; wherein the first light source comprises illumination of suitable wavelengths and power to disinfect the first contaminant.

Some of the presently disclosed embodiments relate to an inspection, disinfection, and documentation device and an associated method of inspection, disinfection, and documentation. Some of the presently disclosed embodiments relate to a hand-held device that incorporates multiple illumination components, multiple corresponding multiwavelength imaging systems, an ultraviolet light disinfection system, and/or a system for controlling the sequence of illumination, and image capture, and/or for guiding an operator through the imaging and disinfection process. According to some embodiments, the presently disclosed system may include methods embodied in software for processing and analyzing the images and for providing safety measures to prevent accidental ultraviolet (UV) light exposure. According to some embodiments, the presently disclosed device enhances the ability of an on-site inspector to visualize invisible contamination residues on surfaces, and for immediate disinfection to ensure an area that people may enter for work, travel, or recreational purposes is safe for the intended use.

According to some embodiments, the presently disclosed system incorporates the combination of detection, disinfection, verification, and documentation including the unique features of: (a) saliva/respiratory droplet imaging; (b) a customer interface with workflow guidance for inspectors and administrators; (c) easy adaptability and integration with Sanitation Standard Operating Procedures (SSOPs); (d) onsite/off-site management through web dashboards.

According to some embodiments, a handheld device presently disclosed may comprise one or more of illumination systems, cameras, optical filters, electronic control systems, system processor modules, battery-operated power supplies, display systems for user interaction, and/or hand-activated controls for user feedback. According to some embodiments, the presently disclosed system may comprise sensors to detect the presence of objects in the imaging and disinfection fields, as well as their distance from the system, and movement and orientation sensors that detect motion and position changes of the handheld device. According to some embodiments, the presently disclosed system may further comprise software for controlling and/or collecting data from cameras, sensors, and illumination systems in response to user commands for imaging and disinfection. According to some embodiments, the presently disclosed system may also provide communication between the presently disclosed device and remotely located data processing computer servers via wired or wireless communication of information for data record storage, cleanliness reports, task management, and/or risk assessment.

According to some embodiments, the presently disclosed system may provide both detection of contamination and immediate disinfection of contamination. Detection of contaminants may be based on imaging of fluorescence, that is characteristic of known contaminants, and that may be on surfaces that humans regularly contact. According to some embodiments presently disclosed, one mode of fluorescence imaging that is of particular advantage is the ability to determine the presence and location of human saliva and respiratory droplets on a surface. In this mode, the surface may be illuminated with ultraviolet light in the wavelength range of 260-290 nm which is used to excite fluorescence of proteins found in human saliva and respiratory droplets. An additional particular advantage of this chosen illumination wavelength is that it is effective for deactivating viruses, killing bacteria, and killing mold/fungi, providing two functions from one source of illumination.

According to some embodiments presently disclosed, another mode of imaging that is of particular advantage is providing illumination using blue/violet wavelengths in the range of 375 nm-425 nm which can be used to excite fluorescence in organic residues, including those containing chlorophyll, porphyrins (often found in bacteria), NADH, FAD, and lipids.

According to some embodiments presently disclosed, the combination of these two modes of imaging, which thereby providing greater specificity of identification and a wider range of contaminant detection is a further advantage of the invention. Another particular advantage of the presently disclosed system according to some embodiments is the employment of multiple cameras with specific wavelength filters in their optical paths that maximize the selectivity of the fluorescence emission of the contamination. The camera sensors may be optimized for adequate sensitivity to the wavelengths of emitted light in the visible and/or ultraviolet wavelength regions.

According to some embodiments, the presently disclosed system delivers a high intensity UV light at the disinfection surface. According to some embodiments presently disclosed, a high intensity of ultraviolet light provides a much shorter deactivation or disinfection time. According to some embodiments presently disclosed, one or more sensors and/or software can disable UV illumination when conditions are unsafe for operators. Examples of unsafe conditions may include: no illumination target in the field of disinfection, activating the UV illumination while the object is too close or too far, activating the UV illumination when it is pointed upwards, moving too quickly, or pointed in a direction where it may encounter other persons, and the accidental pressing of activation controls.

According to some embodiments, a presently disclosed handheld device can be used at varying distances from the object being inspected and is also susceptible to changes in position during the inspection or disinfection due to movement of the device because of operator fatigue or inattention. This can affect whether the surface being disinfected receives adequate UV light energy for disinfection. Other conditions affecting disinfection include viral or bacterial concentration, the size of the contaminated areas, the type of surface that is contaminated, and the kind of contaminant, which can all affect the disinfection energy required. According to some embodiments, a presently disclosed system comprises camera(s) and/or sensor(s) to provide unique information with which to automatically determine the UV light exposure time required to ensure disinfection has been completed at the targeted level, and whether motion or distance changes during the procedure necessitate additional disinfection. According to some embodiments, presently disclosed system can be used to reimage the contaminated area to confirm whether the contamination residues are completely removed.

According to some embodiments, a presently disclosed system may be used to collect and analyze inspection data on a remote server, where records of contamination for different locations and for each facility provide proof of inspection. According to some embodiments, the proof of inspection is videographic. This data may be combined with information about local hazards and/or disease prevalence to provide intelligent dynamic risk assessment associated with each surface in a facility that can be used to update cleaning and inspection processes and guide the device user with updated inspection task lists.

According to some embodiments, a device presently disclosed enhances the ability of an on-site inspector to detect and communicate the presence of saliva stain on an object or in an area. An on-site inspector directs an excitation light in the sensing head of the device into an area of interest. If the targeted saliva stain is present, the excitation light causes the contamination to emit fluorescence. The emitted fluorescent light passes through a narrow spectral band-pass video camera filter and is detected by a video camera mounted in the device sensing head. The video camera transmits the image to a display visible to the on-site inspector. The invention may also recording recording, documenting, and wirelessly communicating the inspection process so that remotely located personnel can view the inspection and respond to the inspection findings in real time.

According to some embodiments, the present invention relates to an inspection tool and an associated method of inspection. Specifically, the invention relates to a specialized hand-held tool that incorporates a lighting device, a corresponding camera system, and a communication means. The tool enhances the ability of an on-site inspector to detect and communicate the presence of saliva stain on a targeted object or in a targeted area. The method can be used to limit the spread of pandemic, zoonotic, and seasonal epidemic influenza.

According to some embodiments, the present invention relates to detecting dried saliva, using for example, fluorescent spectroscopy. Fluorescence spectroscopy may be used to analyze structure, dynamics and functional interactions of proteins. The imaging method presently disclosed may be based on the principle that when a fluorescent material is excited at a particular wavelength, it emits radiation of a longer wavelength which can be recorded. The aromatic amino acid, tryptophan, which is one of the important amino acids in a salivary amylase, an enzyme present in saliva, gives a characteristic emission spectrum at 345-355 nm when excited at a particular wavelength of 282 nm.

Figure 5:
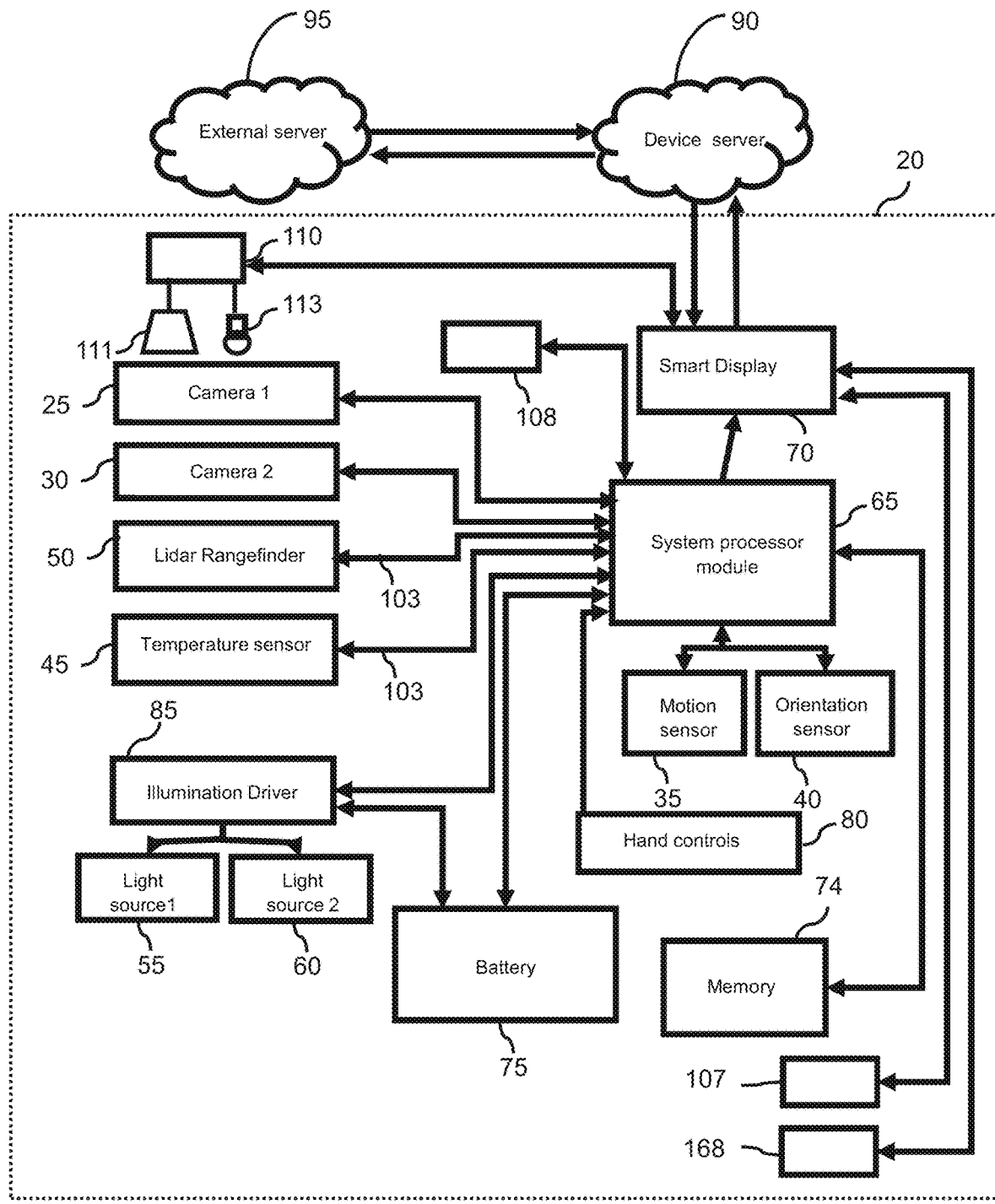
FIG. 5 depicts a block diagram of a device according to some embodiments presently disclosed.

Referring to FIGS. 1-4, a device 10 is shown according to some embodiments presently disclosed. Referring to FIG. 5, a block diagram 20 is shown according to some embodiments presently disclosed. The block diagram 20 depicts some of the components of the device 10 and how they communicate with one another. According to some embodiments presently disclosed, the device 10 is a handheld device. According to some embodiments presently disclosed, the device 10 is part of an inspection and disinfection system. Referring to FIGS. 1-5, according to some embodiment, the device 10 functions as a contamination sanitation inspection and disinfection system (CSI-D).

According to some embodiments presently disclosed, an operator (i.e. user, inspector) uses the device 10 to collect images of a surface to be inspected. According to some embodiments presently disclosed, the device 10 analyzes collected images and identifies one or more contaminated areas on the inspected surface. According to some embodiments presently disclosed, the device 10 shows the one or more contaminated areas to the operator using a display 70 as described below. According to some embodiments presently disclosed, the device 10 allows and/or guides the operator to disinfect the one or more contaminated areas.

According to some embodiments presently disclosed, the device 10 comprises a housing 22 with one or more handles 23. According to some embodiments, the housing 22 of the device 10 comprises additional materials for ruggedization or to provide drop/impact resistance.

According to some embodiments presently disclosed, the device 10 comprises a memory 74 (which may comprise one or more computer readable storage mediums). The memory 74 may comprise high-speed random-access memory and/or non-volatile memory, such as one or more magnetic disk storage devices, flash memory devices, or other non-volatile solid-state memory devices. Access to memory 74 by other components of the device 10, such as one or more system processor modules 65 and a peripherals interface, may be controlled by a memory controller (not shown).

According to some embodiments presently disclosed, the device 10 comprises one or more system processor modules 65. The one or more system processor modules 65 run or execute various software programs and/or sets of instructions stored in memory 74 to perform various functions for the device 10 and to process data. The system processor module 65 may also comprise orientation sensors, motion sensors, global positioning systems, wireless communication systems such as WiFi or Bluetooth systems, cellular network communications systems such 4G, LTE or 5G or similar systems. The system processor module 65 may use these systems to communicate with a device server 90 or it may communicate with the device server via a wired connection through a peripheral interface. The system processor module 65 may also use these systems to communicate with other wireless devices such as cell phones, tablets, smart glasses, other inspection devices or other smart displays as well as RFID systems, barcode readers, fingerprint readers, etc. According to some embodiments, some or all of these components may be implemented on a single chip. According to some embodiments, some or all of these components may be implemented on separate chips.

According to some embodiments presently disclosed, the device 10 comprises an audio circuitry 110, a speaker 111, and a microphone 113. The audio circuitry 110, the speaker 111, and the microphone 113 provide an audio interface between a user (i.e. operator) and the device 10. The audio circuitry 110 receives audio data, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to one or more system processor modules 65 for processing. Audio data may be retrieved from and/or transmitted to memory 74. The audio circuitry 110 may also comprise a headset/speaker jack (not shown). The headset jack provides an interface between the audio circuitry 110 and removable audio input/output peripherals, such as speaker, output-only headphones and/or a headset with both output (e.g., a headphone for one or both ears) and input (e.g., a microphone).

According to some embodiments presently disclosed, the device 10 comprises a display 70. The display 70 may be a touch-sensitive display 70. The touch-sensitive display 70 is sometimes called a "touch screen" for convenience, and may also be known as or called a touch-sensitive display system. In one embodiment, the touch-sensitive touch screen 70 provides an input interface and an output interface between the device 10 and the user. The touch screen 70 is configured to implement virtual or soft buttons and one or more soft keyboards. A display controller receives and/or sends electrical signals from/to the touch screen 70. The touch screen 70 displays visual output to the user. The visual output may include graphics, text, icons, video, and any combination thereof (collectively termed "graphics"). In some embodiments, some or all of the visual output may correspond to user-interface objects, further details of which are described below.

The touch screen 70 has a touch-sensitive surface, sensor or set of sensors that accepts input from the user based on haptic and/or tactile contact. The touch screen 70 and the display controller (along with any associated modules and/or sets of instructions in memory 74) detect contact (and any movement or breaking of the contact) on the touch screen 70 and converts the detected contact into interaction with user-interface objects (e.g., one or more soft keys, icons, web pages or images) that are displayed on the touch screen. In one embodiment, a point of contact between a touch screen 70 and the user corresponds to a finger of the user.

The touch screen 70 may use LCD (liquid crystal display) technology, or LPD (light emitting polymer display) technology, although other display technologies may be used in other embodiments. The touch screen 70 and the display controller may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with the touch screen 70.

A touch-sensitive display in some embodiments of the touch screen 70 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, a touch screen 70 displays visual output from the portable device 10, whereas touch sensitive tablets do not provide visual output.

A touch-sensitive display in some embodiments of the touch screen 70 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 70 may have a resolution of 100 dpi. to 160 dpi. The user may make contact with the touch screen 70 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In addition to the touch screen 70, the device 10 may comprise a touchpad (not shown) for activating or deactivating particular functions. The touchpad is a touch-sensitive area of the device that, unlike the touch screen, does not display visual output. The touchpad may be a touch-sensitive surface that is separate from the touch screen 70 or an extension of the touch-sensitive surface formed by the touch screen.

The one or more system processor modules 65 may be configured to communicate with the smart display 70 to provide information to the user during an inspection or to accept instructions from the operator during an inspection. According to some embodiments, the smart display 70 may be a passive device such as a touch screen display. According to some embodiments, the smart display 70 may be an active device with multiple processing and communication capabilities such as a smartphone or tablet. If the smart display 70 is an active device some of the system software functions may be shared between the one or more system processor modules 65 and the smartphone or tablet. According to some embodiments, the smart display 70 is a smartphone.

The device 10 may also comprise a radio frequency (RF) circuitry 108. The RF circuitry 108 may be configured to receive and transmit RF signals, also called electromagnetic signals. The RF circuitry 108 converts electrical signals to/from electromagnetic signals and communicates with communications networks and other communications devices via the electromagnetic signals. The RF circuitry 108 may include circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 108 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document. According to some embodiments, the radio frequency (RF) circuitry 108 allows the device 10 to communicate with a device server 90 and/or an external server 95.

The device 10 may also comprise a physical or virtual click wheel (not show) and/or one or more controls 80 as an input control device. The user may navigate among and interact with one or more graphical objects (henceforth referred to as icons) displayed in the screen 70 by rotating the click wheel or by moving a point of contact with the click wheel (e.g., where the amount of movement of the point of contact is measured by its angular displacement with respect to a center point of the click wheel) or by activating the one or more controls 80. The click wheel may also be used to select one or more of the displayed icons. For example, the user may press down on at least a portion of the click wheel or an associated button. User commands and navigation commands provided by the user via the click wheel may be processed by an input controller as well as one or more of the modules and/or sets of instructions in memory 74. For a virtual click wheel, the click wheel and click wheel controller may be part of the touch screen 70 and the display controller, respectively. For a virtual click wheel, the click wheel may be either an opaque or semitransparent object that appears and disappears on the touch screen display in response to user interaction with the device. In some embodiments, a virtual click wheel is displayed on the touch screen of a portable multifunction device and operated by user contact with the touch screen.

According to some embodiments presently disclosed, the device 10 comprises a power system 75. The power system 75 powers various components of the device 10. The power system 75 may comprise a power management system, one or more power sources (e.g., battery, alternating current (AC)), a recharging system, a power failure detection circuit, a power converter or inverter, a power status indicator (e.g., a light-emitting diode (LED)) and/or any other components associated with the generation, management and distribution of power in portable devices.

According to some embodiments presently disclosed, the device 10 comprises an optical sensor 25. The optical sensor 25 of the device 10 may be electrically coupled with an optical sensor controller. The optical sensor 25 may comprise charge-coupled device (CCD) or complementary metal-oxide semiconductor (CMOS) phototransistors. The optical sensor 25 receives light from the environment, projected through one or more lens, and converts the light to data representing an image. In conjunction with an imaging module (also called a camera module), the optical sensor 25 may capture visual media (i.e. still images or video). In some embodiments, the optical sensor 25 may be located on the front of the device 10, opposite the touch screen display 70 on the back of the device 10, so that the touch screen display 70 may be used as a viewfinder for either still and/or video image acquisition. In some embodiments, the optical sensor 25 may be located on the back of the device 10 to capture image(s) of the user. In some embodiments, one optical sensor 25 may be located on the back of the device 10 and another optical sensor 25 may be located on the front of the device 10. In some embodiments, the position of the optical sensor 25 may be changed by the user (e.g., by rotating the lens and the sensor in the device housing) so that a single optical sensor 25 may be used along with the touch screen display to capture still and/or video image.

According to some embodiments presently disclosed, the device 10 comprises an optical sensor 30. The optical sensor 30 of the device 10 may be electrically coupled with an optical sensor controller. The optical sensor 30 may comprise charge-coupled device (CCD) or complementary metal-oxide semiconductor (CMOS) phototransistors. The optical sensor 30 receives light from the environment, projected through one or more lens, and converts the light to data representing an image. In conjunction with an imaging module (also called a camera module), the optical sensor 30 may capture visual media (i.e. still images or video). In some embodiments, the optical sensor 30 may be located on the front of the device 10, opposite the touch screen display 70 on the back of the device 10, so that the touch screen display 70 may be used as a viewfinder for either still and/or video image acquisition. In some embodiments, the optical sensor 30 may be located on the back of the device 10 to capture image(s) of the user. In some embodiments, one optical sensor 30 may be located on the back of the device 10 and another optical sensor 30 may be located on the front of the device 10. In some embodiments, the position of the optical sensor 30 may be changed by the user (e.g., by rotating the lens and the sensor in the device housing) so that a single optical sensor 30 may be used along with the touch screen display to capture still and/or video image.

According to some embodiments presently disclosed, the device 10 may also comprise one or more accelerometers 168 as shown in FIG. 5. The accelerometer 168 may perform as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are which are incorporated herein by reference in their entirety. Information may be displayed on the touch screen display 70 in a portrait view or a landscape view based on an analysis of data received from the one or more accelerometers 168.

According to some embodiments, the memory 74 may be configured to store one or more software components as described below.

The memory 74 may be configured to store an operating system. The operating system (e.g., Darwin, RTXC, LINUX, UNIX, OS X, WINDOWS, or an embedded operating system such as VxWorks) comprises various software components and/or drivers for controlling and managing general system tasks (e.g., memory management, storage device control, power management, etc.) and facilitates communication between various hardware and software components.

The memory 74 may be configured to store a system software. The system software may provide data storage for measurements and other information that are transferred from the device 10. The system software may provide system management functions for managing the creation of jobs and task lists that can be implemented using the device 10. The system software may be configured to manage data storage and creation of jobs and task lists for one or more devices 10 for an organization. The system software may comprise firmware software, analysis software, and user interface software.

The memory 74 may also be configured to store a communication module. The communication module facilitates communication with other devices over one or more external ports and also includes various software components for handling data received by the RF circuitry 108 and/or the external port. In one embodiment, the external port (e.g., Universal Serial Bus (USB), FIREWIRE, etc.) is configured for coupling directly to other devices or indirectly over a network (e.g., the Internet, wireless LAN, etc.).

The memory 74 may be configured to store a contact/motion module. The contact/motion module is configured to detect contact with the touch screen 70 (in conjunction with the display controller) and other touch sensitive devices (e.g., a touchpad or physical click wheel). The contact/motion module includes various software components for performing various operations related to detection of contact, such as determining if contact has occurred, determining if there is movement of the contact and tracking the movement across the touch screen 74, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). The contact/motion module and the display controller may also detect contact on a touchpad. The contact/motion module and the controller may further detect contact on a click wheel.

The memory 74 may be configured to store a graphics module. The graphics module comprises various known software components for rendering and displaying graphics on the touch screen 70, including components for changing the intensity of graphics that are displayed. As used herein, the term "graphics" includes any object that can be displayed to a user, including without limitation text, web pages, icons (such as user-interface objects including soft keys), digital images, videos, animations and the like.

The memory 74 may also be configured to store a text input module. The text input module, which may be a component of graphics module, provides soft keyboards for entering text in various applications that need text input.

The memory 74 may be configured to store a GPS module. The GPS module determines the location of the device and provides this information for use in various applications (e.g., to camera module as picture/video metadata).

The memory 74 may be configured to store applications. The applications may comprise one or more of the following modules (or sets of instructions), or a subset or superset thereof: a camera module for still and/or video images; an image management module; a video player module; and/or online video module.

The applications may comprise additional modules (or sets of instructions). For example, other applications that may be stored in memory 74 may include one or more of the following: a contacts module (sometimes called an address book or contact list); a telephone module; a video conferencing module; an e-mail client module; an instant messaging (IM) module; a browser module; a calendar module; search module; notes module; map module; word processing applications; JAVA-enabled applications; encryption; digital rights management; voice recognition; and/or voice replication.

The camera module (in conjunction with, for example, touch screen 70, display controller, optical sensor(s) 25 and/or 30, optical sensor controller, contact module, graphics module, and image management module) may be configured to capture still images or video (including a video stream) and store them into memory 74, modify characteristics of a still image or video, or delete a still image or video from memory 74.

The image management module (in conjunction with, for example, touch screen 70, display controller, contact module, graphics module, text input module, and camera module) may be configured to arrange, modify or otherwise manipulate, label, delete, present (e.g., in a digital slide show or album), and store still and/or video images.

The video player module (in conjunction with, for example, touch screen 70, display controller, contact module, graphics module, audio circuitry 110, and speaker 111) may be configured to display, present or otherwise play back videos (e.g., on the touch screen 70 or on an external, connected display via external port).

The online video module (in conjunction with, for example, touch screen 70, display system controller, contact module, graphics module, audio circuitry 110, speaker 111, RF circuitry 108,) may be configured to allow the user to access, browse, receive (e.g., by streaming and/or download), play back (e.g., on the touch screen 70 or on an external, connected display via external port), upload and/or otherwise manage online videos in one or more file formats.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module may be combined with another module into a single module. The memory 74 may store a subset of the modules and data structures identified above. Furthermore, memory 74 may store additional modules and data structures not described above.

The device 10 may be configured so as to allow operation of a predefined set of functions on the device be performed exclusively through a touch screen 70 and/or a touchpad. By using a touch screen and/or a touchpad as the primary input/control device for operation of the device 10, the number of physical input/control devices (such as push buttons, dials, and the like) on the device 10 may be reduced.

The predefined set of functions that may be performed exclusively through a touch screen and/or a touchpad may include navigation between user interfaces. In some embodiments, the touchpad, when touched by the user, navigates the device 10 to a main, home, or root menu from any user interface that may be displayed on the device 10.

The device 10 as shown in FIG. 5 may comprise more or fewer components than shown, may combine two or more components, or a may have a different configuration or arrangement of the components. The various components shown in FIG. 5 may be implemented in hardware, software or a combination of both hardware and software, including one or more signal processing and/or application specific integrated circuits.

Components shown in FIG. 5 may communicate over one or more communication buses or signal lines 103.

According to some embodiments presently disclosed, the device 10 comprises a motion sensor 35, orientation sensor 40, temperature sensor 45, distance sensor 50, and/or first light sources 55. According to some embodiments presently disclosed, the device 10 may also comprise a second light source 60. According to some embodiments presently disclosed, the device 10 may also comprise hand controls 80 and/or an illumination driver 85.

According to some embodiments presently disclosed, the first light source 55 may provide illumination to excite fluorescence in contaminants that will fluoresce when excited by light in the wavelengths range of 365 nm-410 nm. According to some embodiments presently disclosed, the second light source 60 may provide illumination to excite fluorescence in contaminants that will fluoresce when excited by light in the wavelengths range of 260 nm-290 nm. According to some embodiments, one or both light sources 55, 60 provide light suitable to deactivate or kill at least one of viruses, bacteria, fungi, molds, or other pathogenic sources of disease.

Figure 3:
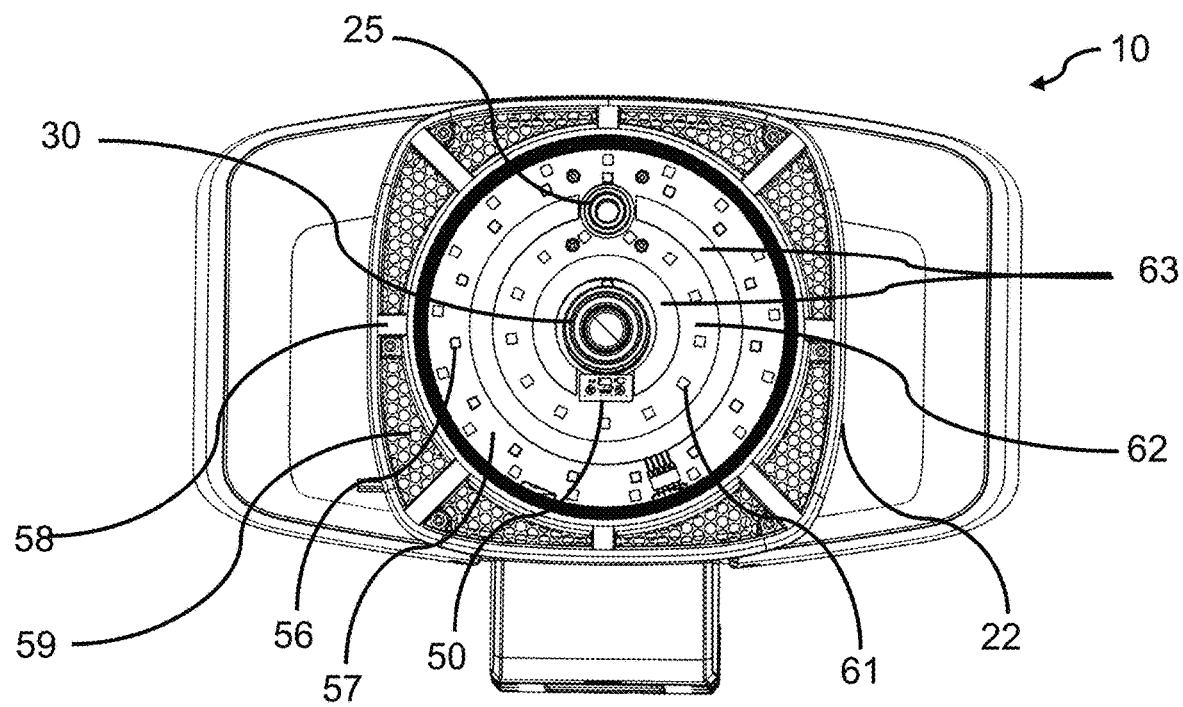
FIG. 3 depicts a front view of the device in FIG. 1.
Figure 4A:
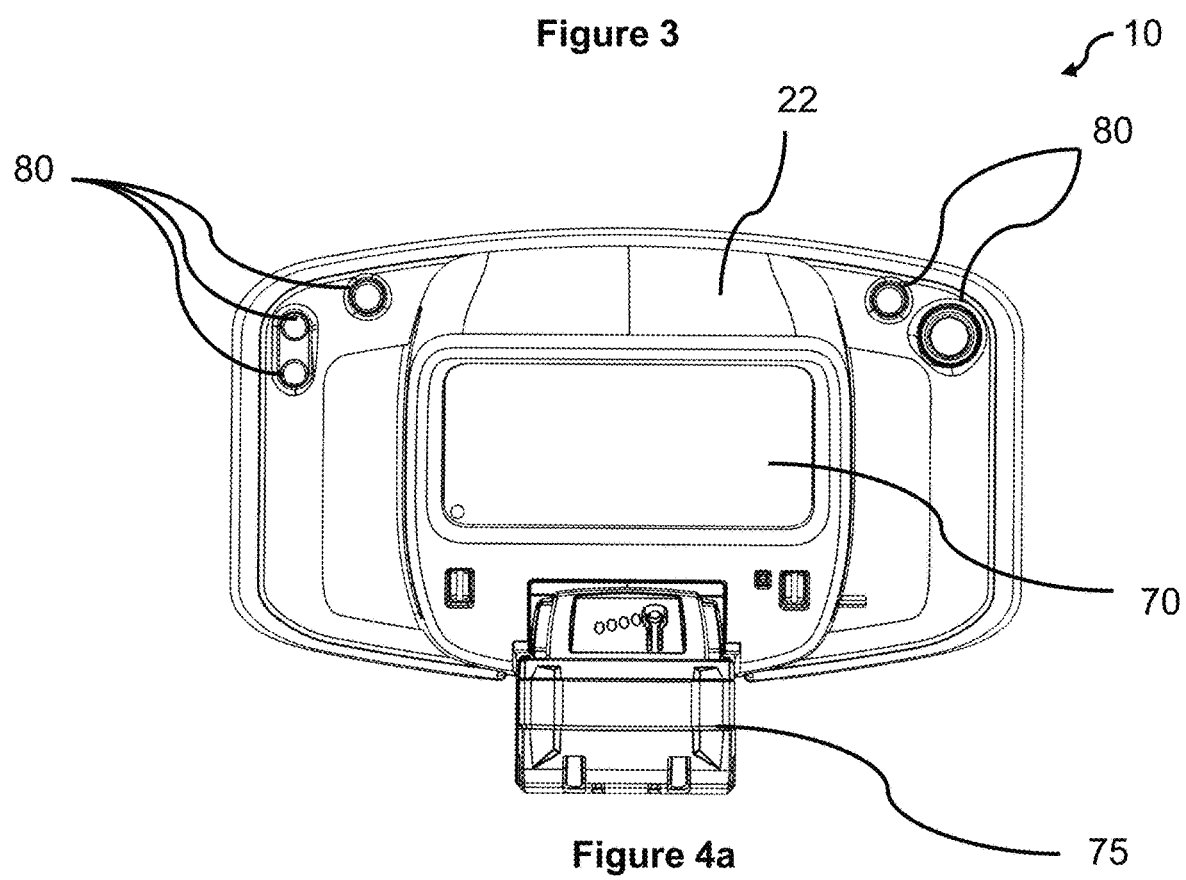
FIG. 4a depicts a rear view of the device in FIG. 1.
Figure 4B:
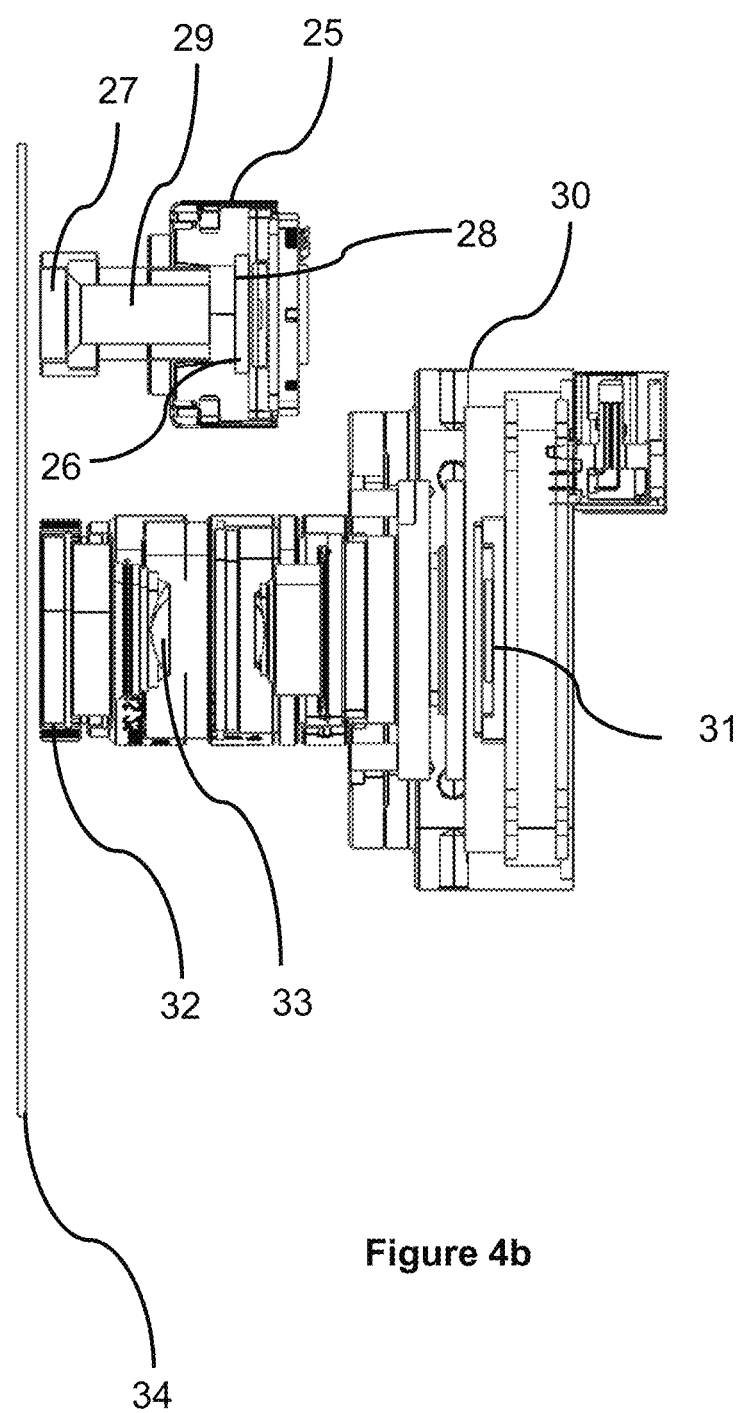
FIG. 4b depicts a cross section view of some imaging components of a device according to some embodiments presently disclosed.

According to some embodiments, the first light source 55 comprises a plurality of Light Emitting Diodes (LEDs) 56 as shown in FIG. 3. According to some embodiments, the LEDs 56 are arranged in a circular pattern. According to some embodiments, the LEDs 56 are arranged in a circular pattern around the camera 30. According to some embodiments, the second light source 60 comprises a plurality of Light Emitting Diodes (LEDs) 61 as shown in FIG. 3. According to some embodiments, the LEDs 61 are arranged in a circular pattern. According to some embodiments, the LEDs 61 are arranged in a circular pattern around the camera 30. It is to be understood that cameras 25 and 30 can be rearranged wherein camera 25 is positioned in the center of LEDs 56 and 61.

According to some embodiments, the illumination driver 85 controls and provides suitable power to the light sources 55, 60. The light sources 55, 60 may be activated by the illumination driver 85 in response to one or more signals from the system processor module 65. According to some embodiments, the light sources 55, 60 are operated in synchronization with the optical sensor(s) (i.e. cameras) 25 and/or 30 to acquire fluorescence image data under appropriate excitation wavelength illumination for each camera 25 and/or 30. The light sources 55, 60 can be operated in continuous or pulsed illumination modes. The pulse mode facilitates background image capture to enhance detectability in brighter ambient light. The illumination driver 85 receives one or more signals from the system processor module 65 to turn the light sources 55, 60 on and off. During fluorescence imaging modes the light sources 55, 60 are turned on and off sequentially via one or more signals from the system processor module 65.

According to some embodiments, the light sources 55, 60 may be lasers, light emitting diodes (LEDs), lamps, or other sources of illumination capable of providing the appropriate wavelengths for fluorescence excitation and/or for disinfection. According to some embodiments, the light source 55 and/or light source 60 are high power LEDs in the wavelength range of UV and blue/violet. According to some embodiments, the light source 55 and/or light source 60 operate in the range of 1 W to 100 W optical power. According to some embodiments, the light source 55 and/or light source 60 provide illumination time for fluorescence imaging of between 1 msec to 200 msec for each excitation wavelength. According to some embodiments, the light source 55 and/or light source 60 provide disinfection time of between 0.1 sec to 60 sec. The actual time of the exposure for either fluorescence imaging or disinfection may be controlled by a system software algorithm which takes into account the task being performed, distance to the surface, illumination light energy, required energy for excitation, required energy for disinfection, and other factors to calculate the illumination and imaging times.

When the task being performed is fluorescence imaging the system sets the illumination time based on the amount of energy the illumination system provides under UV illumination and under blue violet illumination at a known distance that was determined by measurement during a system calibration process. The system software determines the amount of illumination required for detection of a desired contaminant, such as saliva or biological residues or bacteria, from prior knowledge extracted from experimental measurements with known samples.

According to some embodiments, the camera 25 is configured (i.e. optimized) for collection of fluorescence image data that can indicate the presence of specific contaminants on the surface being examined. According to some embodiments, the camera 25 is optimized for collection of fluorescence images from saliva or respiratory droplet residues on the surface being examined. According to some embodiments, the camera 25 comprises an image sensor that has enhanced sensitivity to wavelengths in the range, for example, of 320 nm to 370 nm. The wavelength range of 320 nm to 370 nm is characteristic of the emission of fluorescence from salivary amylase and respiratory droplet proteins such as, for example, tryptophan. According to some embodiments, in order to limit the response of the camera 25 to ambient light, and to make the device 10 more specific to the targeted fluorescence emissions, the device 10 may be equipped with a bandpass filter 27, 32 with sufficient optical density to block the excitation illumination (optical density, OD3 or greater), and other undesired wavelengths, while passing through sufficient fluorescence emission signal to detect contamination.

Figure 8:
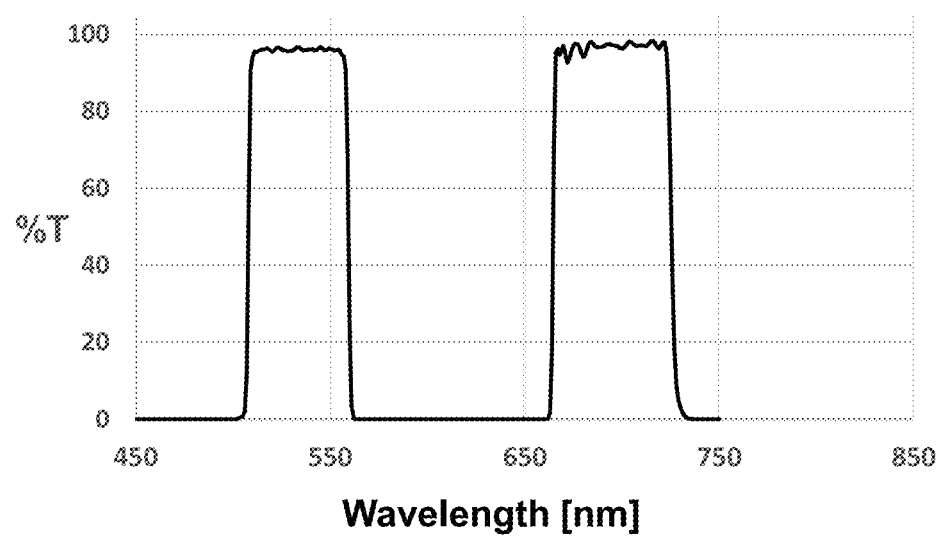
FIG. 8 depicts example wavelength characteristics of double bandpass filter.

According to some embodiments, the camera 30 is configured (i.e. optimized) for collection of fluorescence images from organic residues and other contaminants on the surface being examined. According to some embodiments, the camera 30 comprises an image sensor that has enhanced sensitivity to wavelengths of light in the visible range, for example, of 420 nm to 800 nm. The wavelength range of 420 nm to 800 nm is characteristic of the emission of fluorescence from organic residues and other contaminants such as chlorophyll, porphyrins (often found in bacteria), NADH, FAD, and lipids. NADH stands for "nicotinamide adenine dinucleotide (NAD)+hydrogen (H)." This chemical occurs naturally in the body and plays a role in the chemical process that generates energy. Flavin adenine dinucleotide (FAD) is a redox-active coenzyme associated with various proteins, which is involved with several enzymatic reactions in metabolism. According to some embodiments, in order to limit the response of the camera 30 to ambient light, and to make the device 10 be more specific to the targeted fluorescence emissions, the device 10 may be equipped with a dual or multi bandpass filter 27 (the example wavelength characteristics shown in FIG. 8) with sufficient optical density to block the excitation illumination (OD3 or greater), and other undesired wavelengths, while passing through sufficient fluorescence emission signal to detect contamination. The dual band pass filters may pass selected green and selected red fluorescence emission signals.

According to some embodiments, the camera 25 and/or 30 are equipped with lenses 29, 33 optimized to pass the desired wavelengths and placed so that the fields of view of each camera 25 and/or 30 overlap such that the respective images can be subsequently processed to provide registered image data with a common field of view. According to some embodiments, at least one camera 25 or 30 is used in "view finder mode" to guide the operator when aiming the cameras 25, 30 toward targeted surfaces during inspection and disinfection. In "view finder mode", the cameras 25 or 30 is imaging under ambient light illumination or other light sources integrated in the device 10.

According to some embodiments, the system processor module 65 comprises a computer on an integrated circuit with a Central Processing Unit (CPU), multiple data input and output ports, and peripheral device interfaces with connection to various other components as shown in FIG. 5. The system processor module 65 may host the system software that guides inspections, analyzes data, and communicates with the user (i.e. operator) of the device 10 and one or more external servers 90, 95. The system processor module 65 may provide control of the cameras 25, 30 and the light sources 55, 60 for both imaging and disinfection. The system processor module 65 may manage the timing and synchronization of the light sources 55, 60 with the capture of the fluorescence images by the cameras 25, 30. The system processor module 65 may process the captured images to provide meaningful information to operators and for inspection records.

The system processor module 65 may be configured to communicate with and analyze information from at least one of, the distance sensor 50, the motion sensor 35, the orientation sensor 40 and the image sensor 28, 31 to determine whether conditions are unsafe to activate the light source 55 and/or light source 60. The system processor module 65 may determine the appropriate exposure time for disinfection illumination, to ensure disinfection for a particular target species at a particular distance to the surface to be disinfected, or to control and monitor the disinfection process to determine if during disinfection there was sufficient lack of motion of the handheld device to ensure complete disinfection.

The system processor module 65 may be configured to communicate with and analyze information from at least one of the distance sensor 50, the motion sensor 35, the orientation sensor 40 and the image sensor 28, 31 to determine whether conditions are suitable for image capture such that the image is not blurred, and that sequentially captured images are of the same location on the surface.

According to some embodiments, the distance sensor 50 comprises at least one Light Detection and Ranging (LIDAR) sensor mounted in a forward-facing direction of the device 10 (shown in FIG. 3) and directed towards the field of view of the surface being examined. According to some embodiments, the angular acceptance of the LIDAR sensor can be adjusted programmatically to overlap a desired field of view of the camera systems. According to some embodiments, multiple LIDAR sensors can be used to overlap different portions of the fields of view of the cameras 25, 30. This may be useful if a surface is irregular or of narrow width, because some objects in the field of view may be at greater distance and some objects at nearer distance (i.e. chair with armrests).

The system processor module 65 may be configured to receive and interpret signals from the hand actuated controls 80 of the device 10. Hand actuated controls 80 can include momentary push button switches, on/off push button switches, or multi-axis push button controls that can be used to guide a cursor on the display 70.

According to some embodiments, the device server 90 comprises a computer system connected either wirelessly or by a secure wire or fiberoptic connection to the device 10. According to some embodiments, the device server 90 is a cloud server. The device server 90 may be configured to host the image and inspection history databases for one or more devices 10 and communicates with the system software on one or more devices 10. According to some embodiments, the device server 90 manages the communication of data and reports to and from one or more external servers 95.

According to some embodiments, the one or more external servers 95 may be customer servers or servers providing other data such as local environmental conditions or local disease prevalence. The device server 90 may also host the dynamic risk management algorithms (described in FIGS. 15 and 16). The device server 90 may also host web portals where users of the device 10 and or their managers can view inspection histories, incident reports, device status, inspection status, and where users can setup inspection task lists and perform other management and reporting functions regarding cleanliness status and completeness of the tasks for an inspection task list, multiple inspection task lists for multiple hand held devices or operators, of a facility, or of multiple facilities.

According to some embodiments, the LEDs 56, 61, cameras 25, 30 and/or the distance sensor 50 all positioned behind a protective glass window 34 that is transparent to the wavelengths of light used by the device 10.

Figure 37:
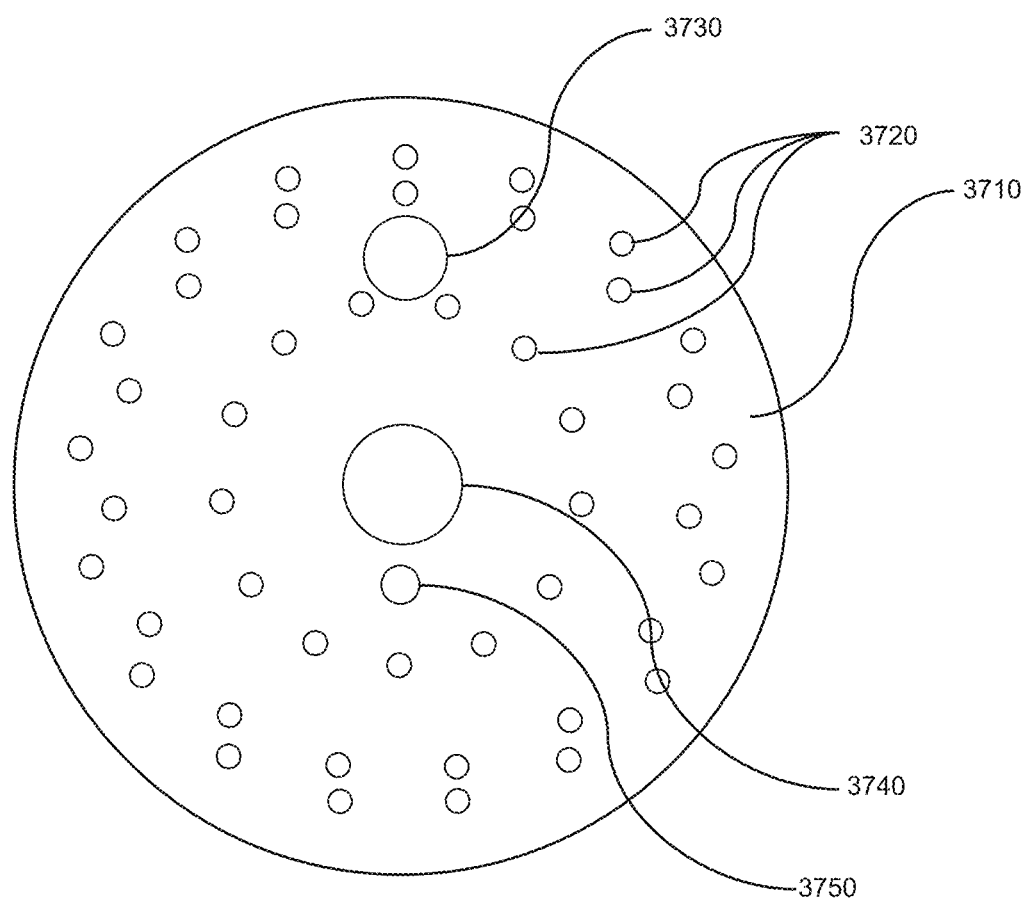
FIG. 37 depicts a protective plate according to some embodiments presently disclosed.

According to some embodiments, as shown in FIG. 37, the LEDs 56, 61, cameras 25, 30 and/or the distance sensor 50 all positioned behind a thin protective plate 3710 where the plate is perforated to allow light to pass through 3720 from each LED 56, 61 and to allow light to pass through 3730, 3740 to the cameras 25, 30 and allow light to pass through 3750 to distance sensors 50. According to some embodiments, the protective plate comprises metal, polymer or other suitable material capable of blocking light. According to some embodiments, the perforations in the protective plate for each LED 56, 61, distance sensor 50, and cameras 25, 30 may be sized to the minimum aperture required for each component's optical function.

Figure 38:
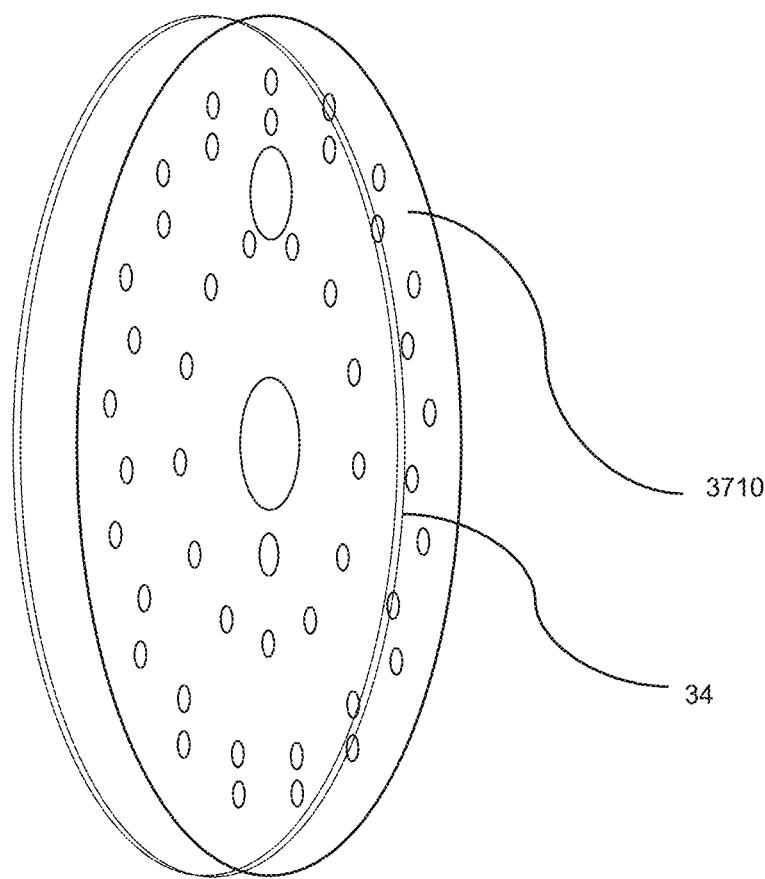
FIG. 38 depicts a protective glass window in combination with a plate according to some embodiments presently disclosed.

According to some embodiments, as shown in FIG. 38 the protective glass window 34 can be used in combination with the perforated plate 3710 or other protective covering. According to some embodiments, the protective glass window and/or protective plate is supported by rings of material 63 such as, for example, cushioning foam, rubber, or silicone placed between the protective glass window and the printed circuit boards 57, 62 on which the LEDs 56, 61 are mounted to provide protection from flexing of the protective glass window which could cause breakage.

Referring to FIGS. 1 and 3, the device 10 may comprise a front bezel 58 surrounding the LED 56, 61. According to some embodiments, the front bezel 58 is configured to hold the protective glass or protective plate or covering and may also provide ventilation for fan driven cooling system 107 of the device 10.

According to some embodiments presently disclosed, the device 10 comprises front ventilation ports 59 directing cooling airflow exhausts from fan driven cooling system 107 away from the operator of the device 10 and towards the potentially contaminated surface, thereby reducing potential contamination hazard for the operator of the device 10.

According to some embodiments presently disclosed, the device 10 comprises a structured illumination system that can project a laser or LED indicator onto the potentially contaminated surface to inform the operator of which areas of inspection are in the field of view of the distance sensor 50 or cameras 25, 30.

According to some embodiments presently disclosed, the system software is fully or partially stored in memory of the device server 90. According to some embodiments presently disclosed, the system software runs on the device server 90.

According to some embodiments presently disclosed, the system software may provide data storage for measurements and other information that are transferred from the device 10. The system software on the device server 90 may provide system management functions for managing the creation of jobs and task lists that can be implemented using the device 10. The system software on the device server 90 may be configured to manage data storage and creation of jobs and task lists for one or more devices 10 for an organization. For example, a company may have five devices 10 at different locations that are managed from a single device server 90. According to some embodiments, the device server 90 may also manage data storage and creation of jobs and task lists for multiple organizations with multiple devices 10.

According to some embodiments presently disclosed, the device server 90 is a cloud server wirelessly connected to one or more devices 10 and providing services to many organizations. The cloud device server 90 may comprise web portals that are accessible through the internet where users or managers can manage one or more devices 10. The system management software on the device server 90 may provide for the creation, storage, and retrieval of inspection and sanitation reports. The system management software on the device server 90 may provide for the creation of a risk index for each inspection task and for analysis of previous inspection and sanitation reports to analyze ongoing risk and apply an updated risk index for each inspection task. The system management software on the device server 90 may provide the ability to communicate with external sources of data. External sources of data can be at least one of an organization server, an institutional server, a server providing data from a government or regulatory body, a server providing data from a public or private source of environmental, health, epidemiological, weather, population, scheduling, transportation, etc. information. The management software on the device server 90 may also provide data to local, regional, national, or international agencies or regulatory bodies.

The device server 90 may communicate task management information and collect data via wired or wireless methods to the system software on the device 10. The system software can communicate reports and measurement data and device 10 system status to the device server 90. The system software may comprise firmware software, analysis software, and user interface software.

The user interface software provides information and control screens on the display 70 to guide a user (i.e. operator) through the inspection and the inspection task list. According to some embodiments, the user interface software displays options to the operator via the display 70 and accepts input from the operator via either the display 70 or the hand controls 80 on the smart display and/or accepts input from the operator via the smart display 70 and the hand controls 80 on the device. According to some embodiments, the user interface software provides for communication of inspection tasks, inspection status and inspection results to the device server 90.

The firmware software may be directly connected to and controls the hardware components of the device 10. The user interface software provides information to and interprets commands from the device 10 operator. The analysis software continuously analyzes sensor measurements 35, 40, 50, 45, analyzes image data, and provides information to the user to guide the inspection. The analysis software also interprets measurements and continuously assesses safety conditions and disables UV illumination in unsafe conditions. The analysis software also dynamically interprets measurements and calculates the duration of UV illumination required for effective disinfection for each task. It also monitors the disinfection to determine if it was completed or if disinfection needs to be repeated.

The firmware software prepares the cameras 25, 30 and the light sources 55, 60 for image capture by setting appropriate parameters for each camera including exposure time, camera gain, camera offset, pixel binning, and other programmable settings of the camera appropriate for capturing the desired image. The firmware software also sets the on-times and off-times for each source of illumination.

Figure 6:
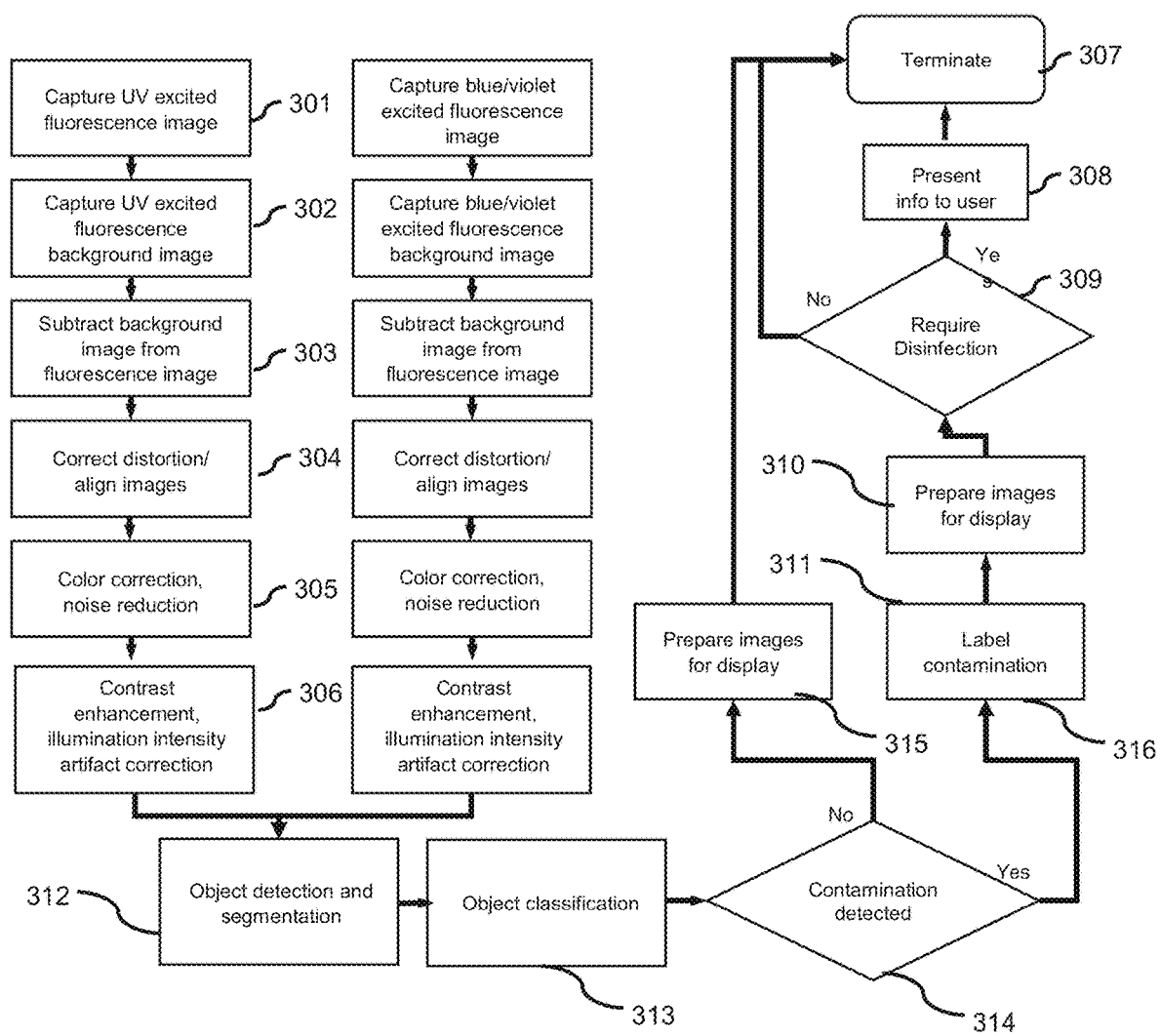
FIG. 6 depicts image processing and analysis according to some embodiments presently disclosed.

According to some embodiments presently disclosed, upon initiation of image capture by the user, the firmware software begins a sequence of operations to capture, for example, four images, including a UV excited fluorescence image, a background image associated with the UV excited fluorescence image, a blue/violet excited fluorescence image, and a background image associated with the blue/violet excited fluorescence image. The background images can be captured at the same or at different exposure times compared to their associated fluorescence images. If the background images are captured at different exposure times, their intensities may be scaled to correct for the difference in exposure times. For example, if the exposure time of the background image is half the time of the fluorescence image, the intensities would be multiplied by two to correct for the difference in exposure time. After the images are captured in the system processor module 65 memory, image processing and analysis can begin as shown in FIG. 6.

According to some embodiments presently disclosed, the background image related to each fluorescence image 301 is scaled to correct for exposure time, if required, and subtracted from the fluorescence image to produce a background-corrected fluorescence image 303. The background-corrected fluorescence images may comprise at least one image that is created from the fluorescent light emitted in a particular wavelength band when excited by one of the illumination sources. A wavelength band has a starting wavelength and an ending wavelength and includes light of all wavelengths between the starting wavelength and the ending wavelength. There can be one or more wavelength bands collected in a single image. There can also be multiple images with one or more wavelength bands collected. The images can be collected from one or more cameras 25, 30. The wavelength bands of light passing through to the camera 25, 30 can be selected by at least one optical filter 27, 32 placed in the image path of the camera 25, 30. The optical filter may also be integrated with the image sensor 26, 31 of the camera 25 or 30. The optical filter 28 integrated with image sensor 26 can be a single uniform filter such as an infrared cut off filter, or it can be a mosaic filter such as a Bayer filter. A uniform filter has the same optical properties for wavelength selection across the area of the sensor 26, 31. A mosaic filter comprises a patterned arrangement of optical filters with different optical properties for wavelength selection providing different wavelength bands of light to different pixels of the image sensor 26, 31. An example of a mosaic filter may be, for example, the Bayer filter which comprises an array of red, green and blue filters that is commonly employed in color digital camera sensors. According to some embodiments, at least one camera 25 or 30 in the device 10 may comprise both a uniform filter and a mosaic filter in the optical path. According to some embodiments, the uniform filter comprises at least one wavelength band that passes a desired fluorescence signal, and that otherwise blocks undesired fluorescence excitation light wavelengths and or background illumination wavelengths. According to some embodiments, the uniform filter comprises at least two wavelength bands that pass desired fluorescence signals, and that otherwise block undesired fluorescence excitation light wavelengths and or background illumination wavelengths. According to some embodiments, the uniform filter comprises at least two wavelength bands that pass desired fluorescence signals, and that otherwise block undesired fluorescence excitation light wavelengths and or background illumination wavelengths.

According to some embodiments, the mosaic filter comprises at least two wavelength bands that pass desired fluorescence signals. According to some embodiments, the mosaic filter comprises at least three wavelength bands that pass desired fluorescence signals. According to some embodiments, the mosaic filter comprises at least between three and nine wavelength bands that pass desired fluorescence signals. According to some embodiments, optical filtering systems may include electronically controlled spectral filters such as acousto-optic tunable filters (AOTF), liquid crystal tunable filters (LCTF), and other electromechanical of wavelength selection by (linear variable spectral filters or filter wheels).

According to some embodiments, the two cameras 25, 30 are disposed beside (i.e. adjacent to) one another such that their imaging paths are parallel or nearly parallel and the fields of view (FOV) of the images overlap one another and include the portions of the field of view that are illuminated by fluorescence excitation light from light sources 55, 60. The cameras 25, 30 may comprise sensors optimized for detection of a particular wavelength range of fluorescent light and optimized for the lenses and optical filtering systems of that camera. According to some embodiments, one of the cameras 25 or 30 is optimized for the detection of ultraviolet fluorescence emissions and the blocking of UVC fluorescence excitation, as well as other wavelengths in the visible light range, and a second camera 25 or 30 is optimized for the detection of at least two wavelength bands of fluorescence emission in the visible and near infrared range and the blocking of blue-violet excitation light. According to some embodiments, camera 25 comprises a camera sensor with a mosaic filter 28 and a bandpass filter 27 that passes the at least two fluorescence wavelength bands in the visible and near infrared light wavelength range and blocks the blue-violet excitation light.

According to some embodiments, the images from the cameras 25, 30 may be co-registered. According to some embodiments, the images from the cameras 25, 30 may require distortion correction 304 if the cameras 25, 30 have different magnifications, or different sensor pixel sizes, or cause images to have image distortion such as barrel distortion or pincushion distortion. In barrel distortion, image magnification decreases with distance from the optical axis. The apparent effect is that of an image which has been mapped around a sphere (or barrel). Fisheye lenses, which take hemispherical views, utilize this type of distortion as a way to map an infinitely wide object plane into a finite image area. In a zoom lens, barrel distortion appears in the middle of the lens's focal length range and is worst at the wide-angle end of the range. In pincushion distortion, image magnification increases with the distance from the optical axis. The visible effect is that lines that do not go through the center of the image are bowed inwards, towards the center of the image, like a pincushion.

According to some embodiments, cameras 25, 30 are calibrated for different distances of imaging to provide for the correction of distortion and the co-registration of images which can have different correction and co-registration algorithm parameters as a function of the distance between the cameras 25, 30 and the surface being imaged. This calibration process may be performed by capturing a series of images at varying distances from the cameras 25, 30 and the analysis of the images at each distance to provide an image correction process for each camera 25, 30 at each distance. According to some embodiments, the image correction process comprises applying a formula for at least one of: correcting barrel distortion or pincushion distortion, adjusting the sizes of the images, laterally translating the images, or rotating the images so that all images are co-registered.

After image distortion correction and image co-registration, the images can be prepared for analysis. According to some embodiments, preparation for analysis comprises at least one of noise reduction 305, color correction, contrast enhancement 306, and adjustment for illumination intensity non-uniformity 306, or correction for image capture with different exposure times. When images are captured sequentially under different illumination conditions such as illumination by one or more light sources or under the absence of illumination, the system software may control the timing of the image capture and the illumination such that the illumination is synchronized with the appropriate camera system for image capture of both fluorescence excitation images and background images.

Figure 7:
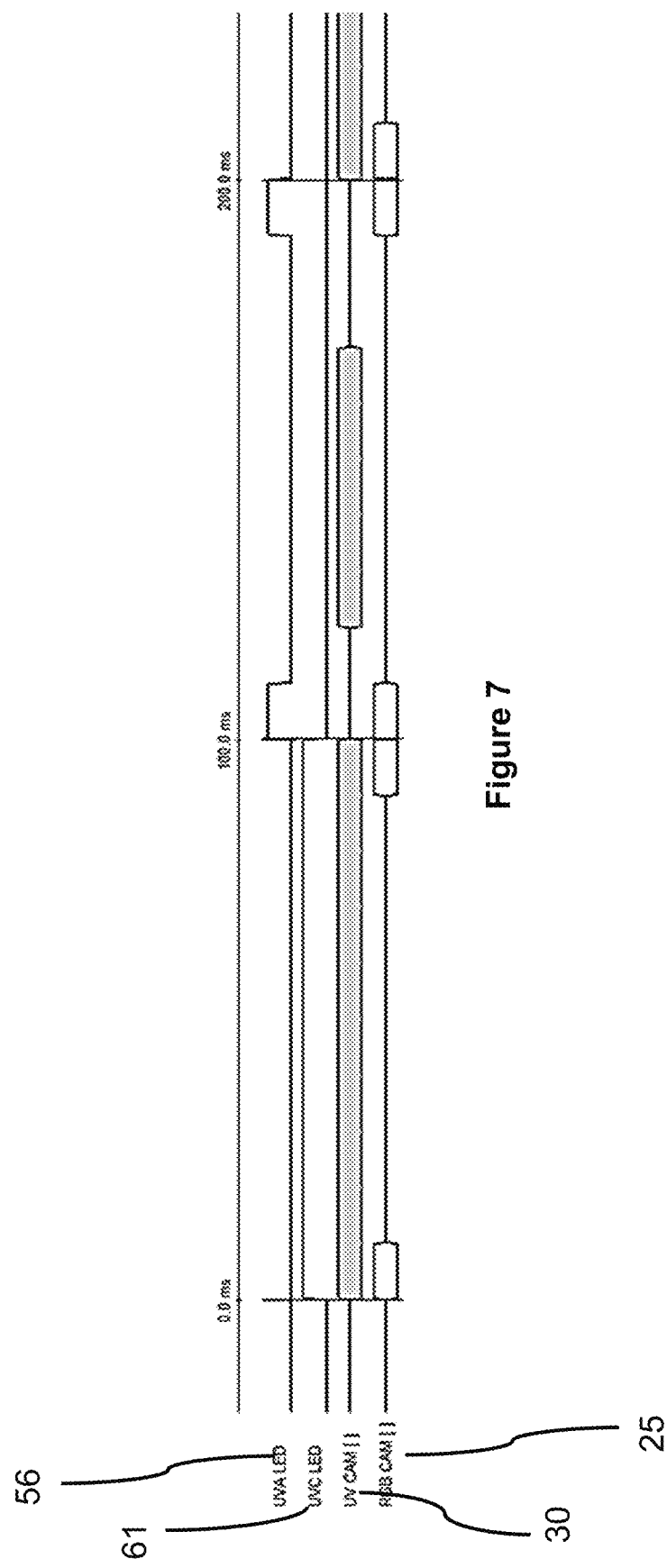
FIG. 7 depicts timing diagram according to some embodiments presently disclosed.

FIG. 7 shows a timing diagram according to some embodiments presently disclosed with two light sources 55, 60 and two cameras 25, 30. The duration of the on and off periods for the light sources 55, 60 or cameras 25, 30 image acquisition time may be varied for different imaging tasks or for different arrangements of cameras and can be adjusted to balance sensitivity of detection with speed of image acquisition. According to some embodiments, the end result of this sequence of illumination and image capture triggering is four captured images. These four images may include: one blue/violet excitation fluorescence image in the emission range from 500 nm to 565 nm (shown in FIG. 8), one blue/violet excitation fluorescence image in the emission range from 660 nm to 735 nm (shown in FIG. 8), one background image from the same camera system with the blue violet excitation illumination off and one UVC excitation fluorescence image in the emission ranges from 300 nm to 400 nm.

According to some embodiments, the camera 25 used for blue/violet fluorescence excitation imaging is a color camera, with a mosaic-filtered sensor. The camera 25 can be operated in a view finder mode where the illumination light sources are not enabled, and the camera exposure can be adjusted to provide optimal images from the camera 25 which can be further processed to provide a streaming image of the camera field of view to an operator to assist aiming and positioning of the device 10 for fluorescence imaging or disinfection.

When the device 10 is in position for inspection, the system operator can activate the inspection imaging sequence that provides the fluorescence and background imaging for processing and analysis. According to some embodiments, analysis comprises object detection, segmentation, and classification to extract contamination information. The object detection 312 can employ intensity-based or morphology-based algorithms for identifying the surface areas with fluorescence emission. The image segmentation algorithm can be based on threshold optimization using image intensity histogram analysis. Classification methods can comprise comparison of the segmented objects across the images. An object may appear in only one fluorescence image or it may appear in multiple fluorescence images. By comparing the relative fluorescence intensity response of the segmented object at multiple wavelengths the object can be classified by comparison to the relative responses of known types of contamination.

FIGS. 9-13 depict examples of fluorescence responses of different contaminants that can be detected by the device 10.

Figure 9:
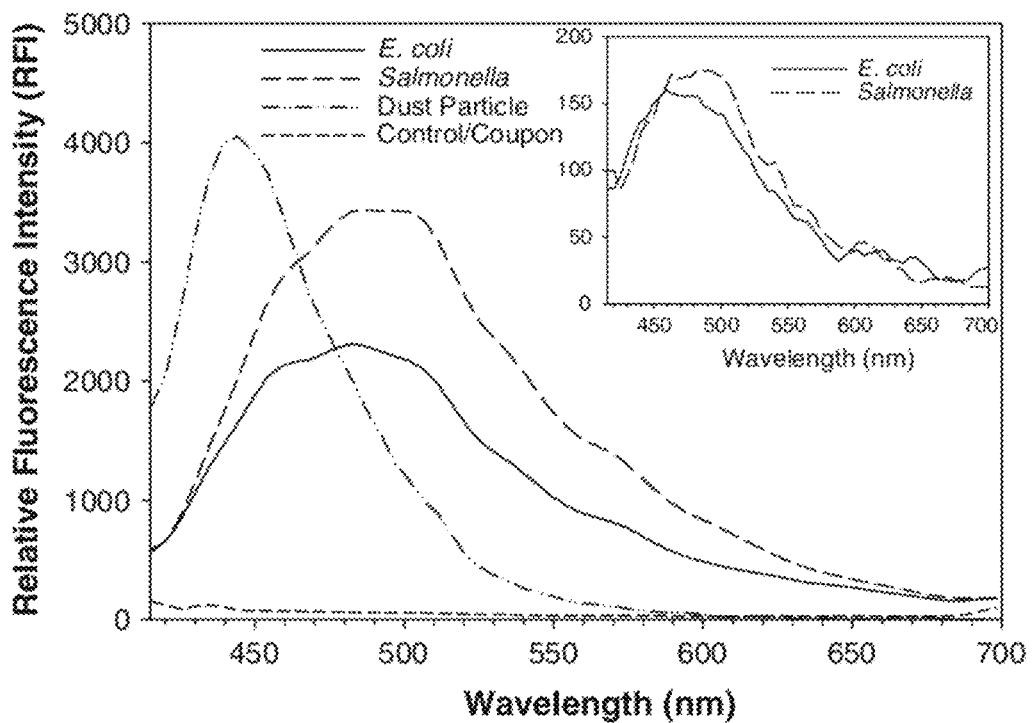
FIG. 9 depicts a graph of the fluorescence emissions of *salmonella* and *E. Coli* as known in the art.

FIG. 9 depicts a graph of the fluorescence relative intensity responses across multiple wavelengths of the *E. Coli* and *Salmonella* bacteria pathogens, as well as that of surface dust and a control biofilm without the bacteria. Comparing the relative response at each imaging wavelength band for a given excitation wavelength to the integrated response for that wavelength band in the known relative spectral response of these pathogens provides a quantitative measure of likelihood that the object in the image may or may not have the pathogen present. More details can be found in an article by Jun W, Kim M S, Lee K, Millner P, Chao K. Assessment of bacterial biofilm on stainless steel by hyperspectral fluorescence imaging. Sensing and Instrumentation for Food Quality and Safety. 2009 Mar. 1; 3(1):41-8, which incorporated herein by reference.

Figure 10:
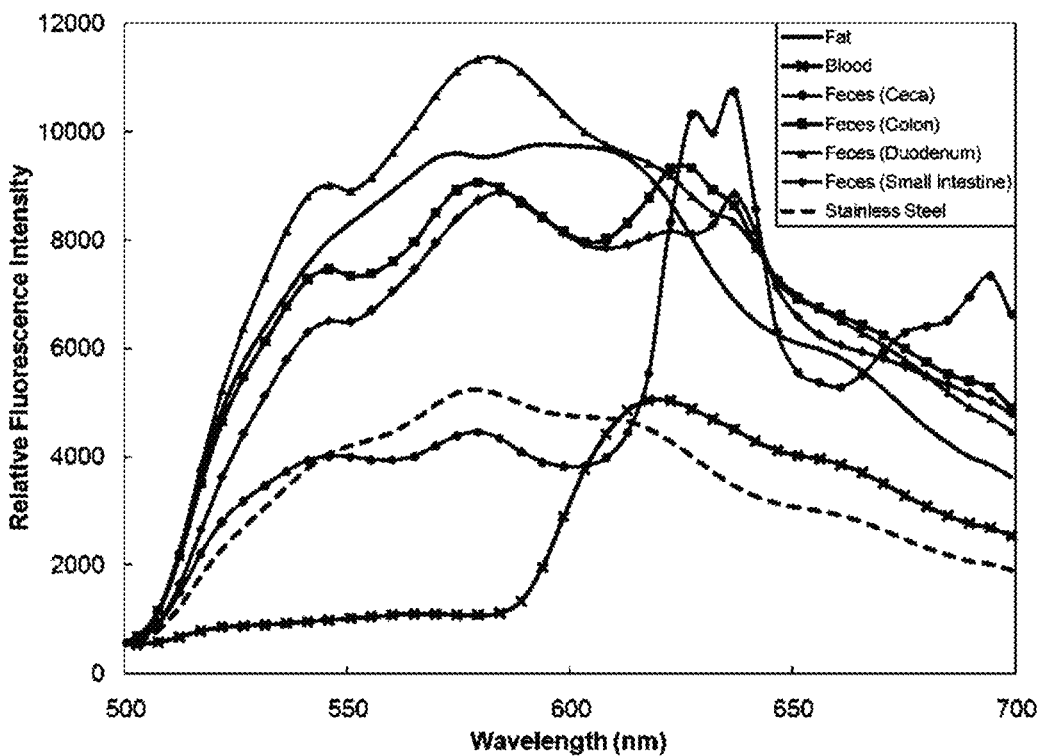
FIG. 10 depicts fluorescence relative intensity responses across multiple wavelengths for several organic residues as known in the art.

Similarly, FIG. 10 depicts an example of fluorescence relative intensity responses across multiple wavelengths for several organic residues as well as stainless steel, a common background surface in food preparation areas. These organic residues include fat, blood, and several kinds of feces from poultry carcasses. Comparing the relative response at each imaging wavelength band for a given excitation wavelength to the integrated response for that wavelength band in the known relative spectral response of these organic residues provides a quantitative measure of likelihood that the object in the image may contain that particular organic residue. More details can be found in an article by Qin J, Chao K, Kim M S, Kang S, Cho B K, Jun W. Detection of organic residues on poultry processing equipment surfaces by LED-induced fluorescence imaging. Applied engineering in agriculture. 2011; 27(1):153-61, which incorporated herein by reference.

Figure 11:
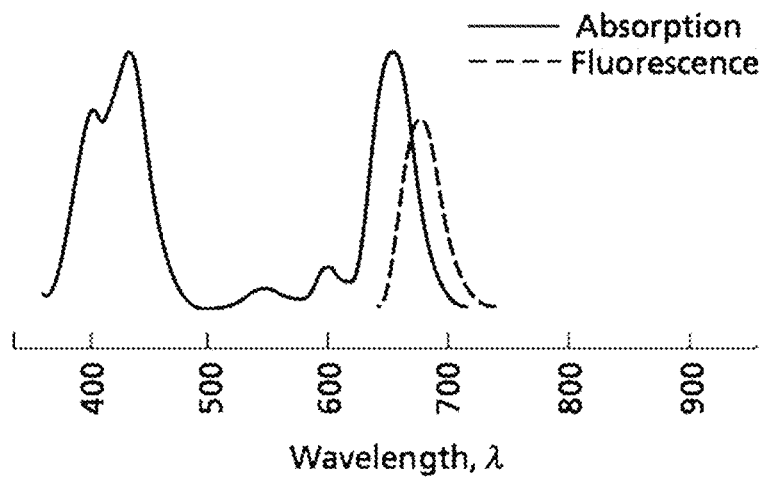
FIG. 11 depicts excitation and emission spectral fluorescence responses of chlorophyll across multiple wavelength as known in the art.

FIG. 11 depicts an example of relative excitation and emission spectral fluorescence responses across multiple wavelengths for chlorophyll. Chlorophyll residues are found in vegetables and fecal matter and can be a source of evidence that a surface is not clean. Comparing the relative response at each imaging wavelength band for a given excitation wavelength to the integrated response for that wavelength band in the known relative spectral response of chlorophyll residues provides a quantitative measure of likelihood that the object in the image may contain chlorophyll residue. More details can be found in an article by Fernandez-Jaramillo A A, Duarte-Galvan C, Contreras-Medina L M, Torres-Pacheco I, Romero-Troncoso R D, Guevara-Gonzalez R G, Millan-Almaraz J R. Instrumentation in developing chlorophyll fluorescence biosensing: A review. Sensors. 2012 September; 12(9):11853-69, which incorporated herein by reference.

Figure 12A:
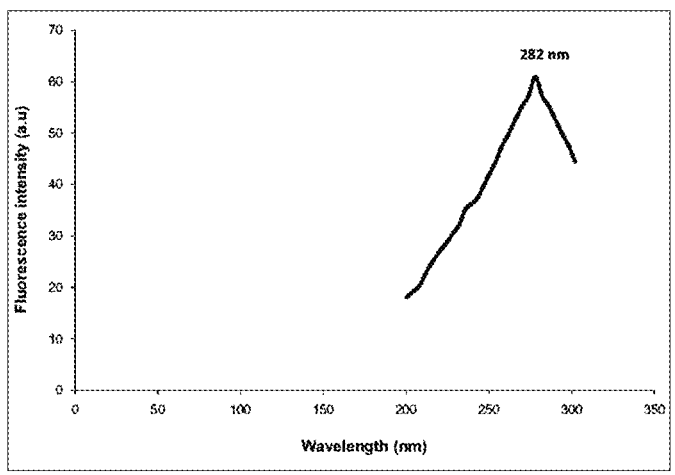
FIG. 12a-b depict relative excitation and emission spectral fluorescence responses of saliva across multiple wavelengths as known in the art.
Figure 12B:
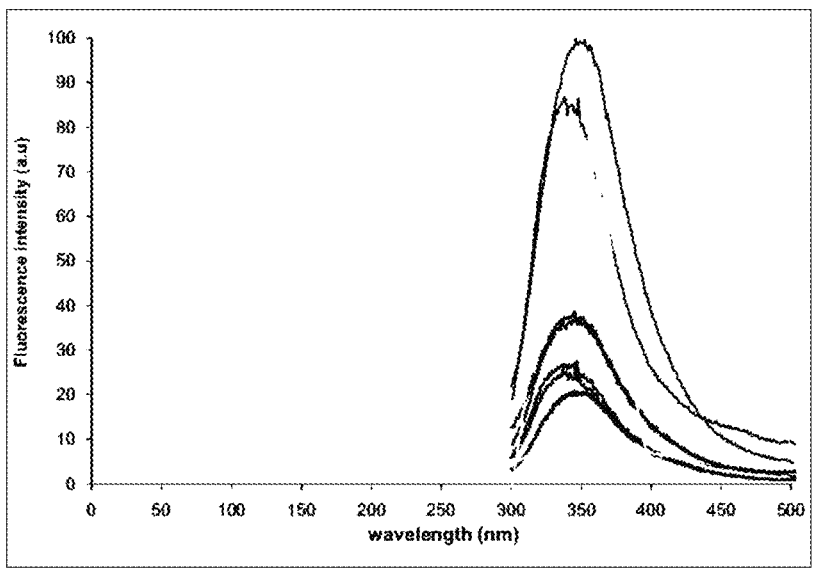

FIGS. 12a-b depict an example of relative excitation and emission spectral fluorescence responses across multiple wavelengths for human saliva. Saliva residues can be a source of multiple bacteria, pathogenic viruses and can provide evidence that a surface is not clean. Comparing the relative response at each imaging wavelength band for a given excitation wavelength to the integrated response for that wavelength band in the known relative spectral response of saliva and respiratory droplet residues provides a quantitative measure of likelihood that the object in the image may contain saliva residue. More details can be found in an article by Nanda K D, Ranganathan K, Umadevi K M, Joshua E. A rapid and noninvasive method to detect dried saliva stains from human skin using fluorescent spectroscopy. Journal of Oral and Maxillofacial Pathology: JOMFP. 2011 January; 15(1):22, which incorporated herein by reference.

Figure 13:
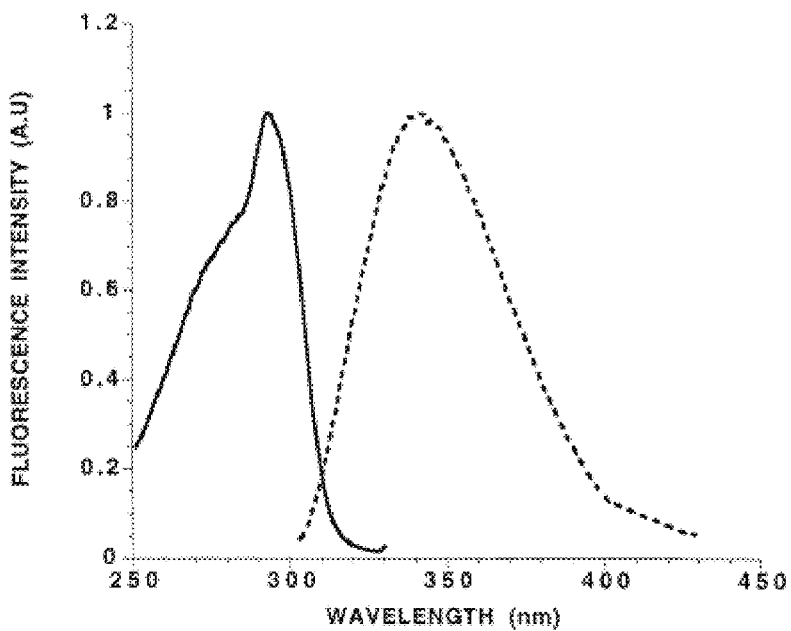
FIG. 13 depicts relative excitation and emission fluorescence spectral responses across multiple wavelengths as known in the art.

FIG. 13 depicts an example of relative excitation and emission fluorescence spectral responses across multiple wavelengths for tryptophan, an amino acid which is an essential building block for multiple food proteins as well as human proteins that can be found in saliva and respiratory droplets. More details can be found in an article by Brancaleon L, Lin G, Kollias N. The in vivo fluorescence of tryptophan moieties in human skin increases with UV exposure and is a marker for epidermal proliferation. Journal of investigative dermatology. 1999 Dec. 1; 113(6):977-82, which incorporated herein by reference.

The examples of contamination described above and shown in FIGS. 9-13 are all difficult to detect visually without the device 10, especially when they are at low concentrations, which can result in a surface having residual contamination despite cleaning, because the cleaner cannot detect their presence.

The classification algorithm presently disclosed may comprise spatial analysis of the objects in the image field including object size, object shape, and distribution pattern. The distribution pattern and size for respiratory droplets or saliva deposited on the surface by sneezing or coughing will be different from the distribution pattern and size for organic residues cause by food contamination, spills, or by touching or wiping a surface with dirty hands or held objects such as tissues or dirty cleaning cloths. Classification algorithm uses distribution pattern and object shapes of the objects to determine that they are spray pattern characteristics of respiratory droplets during sneezing or coughing, or whether the distribution pattern is more characteristic of a hand smear or a food residue. The classification algorithm calculates the probability of similarity to at least one of those types of contaminations.

The classification algorithm presently disclosed can also compare relative fluorescence emission or excitation responses of the objects in the image and compare them to known responses of known contaminants and determine a probability of similarity of at least one of those types of contaminations. The classification algorithm calculates the probability of similarity of relative fluorescence emission to at least one of those types of contaminations.

The classification algorithm presently disclosed can also compare relative fluorescence emission or excitation responses or spatial analysis of objects in the image field to classify objects other than contamination, such as reflections or background fluorescence from surfaces or artifacts. By comparing the presence of objects from prior images of different surfaces artifacts of the imaging system or process can be identified and classified as not relevant to contamination.

As objects are classified, the system software may create a table of data associated with each object comprising location of the object in the image, a binary mask of the object, measures of the area of the object, the size and orientation of the major and minor axes of an ellipse approximating the object, the average fluorescence response of the object at each fluorescence emission wavelength band and the calculated probability that the object comprises at least one specific contamination type or comprises an artifact or a false positive object. From this information the system software can determine if the object is contamination or not. The threshold for determining whether the object is a contamination can be adjusted for greater or lesser sensitivity in order to minimize false positives. The determination of whether or not an object is contamination can be represented as a binary decision such as yes or no, or it can be represented as a probability that an object is a contamination such as a percentage probability or other indication of probability for example none, low, medium, high or it can be represented graphically in the form of a color code or a sliding bar indicator. Once an object is classified, it can be labeled in the image that is stored or presented to the user with an overlay, an outline around the object, or a text or marker tag on or near the object. The overlay, outline, text, or marker tag can be color coded to indicate different types of contamination.

The presentation of information to the operator may be accomplished via a visual display that guides the user during the inspection process and during the scanning part of the process provides a stream of the image data described above. When contamination is detected the image display will provide a visual and/or audible or vibrating alarm to indicate to the user to stop and focus imaging on the area where the contamination is identified. The display will present information about the detected object via overlay, outline, text, or marker tag that can also be color coded 308. The display 20 may then prompt the user to disinfect the area if desired. The user can proceed to disinfection or make a judgment that disinfection is not required and skip the disinfection process and continue with the inspection.

If disinfection is elected, the system software calculates the amount of UV light required to disinfect the surface. Disinfection efficiency can be proportional to a number of factors. These include the amount of energy that is delivered to the surface to be disinfected, the size and thickness of the contamination on the surface, whether the contamination is dry or in the form of liquid or biofilm, the nature of the surface to be disinfected (smooth, porous, metal, fabric, optical absorption or reflectance properties of the surface, etc.) as well as the type of contaminant or the species of concern that may be present in the contaminant. Different species can require more or less UV energy for effective disinfection. Effective disinfection is defined as the percentage of pathogen killed or de-activated. Often this percentage is represented in the form of a "Log reduction" or an order of magnitude. For example, a 1-log reduction corresponds to inactivating 90 percent of a target microbe with the microbe count being reduced by a factor of 10; a 4-log reduction corresponds to inactivating 99.99 percent of a target microbe with the microbe count being reduced by a factor of 10,000.

The system software calculates the UV disinfection exposure time required by looking up the amount of energy required in Joules per square meter and looking up the amount of energy in Joules per square meter per second that the UV illumination of the handheld system delivers at the distance from the handheld system of the surface to be disinfected. The amount of energy the UV illumination in the handheld system delivers is determined during a calibration procedure where the disinfection energy delivered by the system is measured at various distances from the handheld system. The system software calculates the amount of time required to deliver sufficient disinfection energy to effectively disinfect the pathogen species of concern at the desired log reduction level, and at the distance of the device from the surface to be disinfected.

The distance of the device 10 is determined from the measurements of the distance sensor 50 or other distance measuring system. When disinfection begins the system software automatically controls the duration of the illumination exposure time for disinfection. It is important that the operator holds the system in a still position during the disinfection period. The software system monitors at least one of: the motion sensors 35, camera 25, 30, and orientation sensors 40. If the system software monitoring at least one of these sensors indicates that the handheld device is no longer illuminating or only partially illuminating the area to be disinfected, the operator will be notified that the disinfection is incomplete and needs to be redone.

Figure 14:
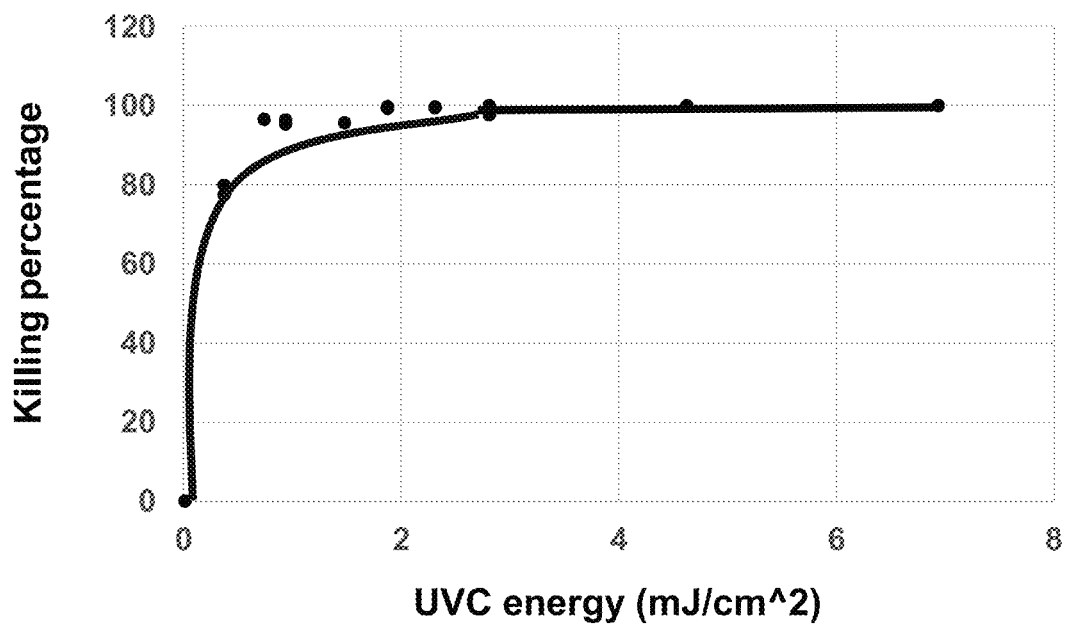
FIG. 14 depicts a graph of killing percentage of bacteria with UVC.

FIG. 14 depicts a killing percentage of bacteria with UVC increasing energy (mj/cm^2) at 275 nm.

According to some embodiments, the presently disclosed device 10 uses ultraviolet illumination to both detect and to disinfect contaminants on surfaces. The same ultraviolet light that can kill bacteria and inactivate viruses, can also cause damage to human cells and tissue (e.g., eye and skin). According to some embodiments, the presently disclosed device 10 may instruct users in the safe handling of the device 10 so that they do not inadvertently expose themselves or others to UV radiation.

According to some embodiments presently disclosed, intelligent and automated safety measures are provided to decrease the risk of accidental exposure to UV light. These safety measures comprise sensors, user controls, and software algorithms that detect if the device is in a potentially unsafe situation and disable the UV illumination until the situation is safe again.

According to some embodiments presently disclosed, the sensors include at least one of distance measurement sensors 50, orientation sensors 40, motion sensors 35, and image sensors of camera systems 25, 30. According to some embodiments presently disclosed, system software safety algorithm (described in FIG. 36) monitors 3610, 3620, 3630 the state of the sensors 50, 35, 40 and if any one of, or a combination of, sensor values indicate an unsafe situation, the UV illumination is disabled, and the user is notified by at least one of an audible or visual signal. According to some embodiments presently disclosed, to prevent accidental activation of the UV illumination the system software safety algorithm monitors 3640 the state of the user controls 80 so that the UV illumination is disabled unless the user has both hands holding the device and simultaneously presses the control buttons on the right and left handles of the device. If one or both of the control are released, the UV illumination is disabled.

According to some embodiments presently disclosed, cameras 25, 30 may be used as rangefinders (i.e. distance sensors) by using technique of stereogrammetry or by using autofocus measurement system built into the cameras 25, 30.

According to some embodiments presently disclosed, the safety algorithm monitoring the orientation sensor 40 may disable UV illumination because it the device 10 is in an common position (i.e. for example pointing up towards the sky) or has additional safety considerations. For these situations, the system software may provide an override option allowing the operator to proceed while acknowledging the risk and the need for extra caution.

According to some embodiments presently disclosed, device 10 multiple distance sensors 50 (for example LiDAR) that may be directed towards different areas of imaging field. This provides multiple points of distance measure for calculating safety and dosimetry and may be of particular advantage if the surface being inspected has a narrow width or a topography that is not consistent in distance from the handheld device. According to some embodiments presently disclosed, a combination of imaging stereogrammetry and range finder sensing can identify the true depth of a field of view with irregular shape.

According to some embodiments presently disclosed, the device 10 comprises a clear window (not shown) to protect the cameras 25, 30 and light sources 55, 60 from being touched by the operator of the device 10. This clear window cannot be ordinary glass because most glass does not transmit wavelengths of light in the UV wavelength regions that are most effective for disinfection and for ultraviolet fluorescence detection of the potential contaminants (e.g. saliva and respiratory droplets at 300-400 nm). According to some embodiments presently disclosed, the clear window is fabricated from fused silica and coated with antireflection coatings that transmit the UV and visible light CSI-D uses for detection and disinfection efficiently.

According to some embodiments presently disclosed, the device 10 comprises a thin disk of material such as, for example, metal, or other suitable material is placed in front of the illumination sources 55, 60 and camera lenses 25, 30. This thin disk may be perforated with a series of apertures that protect the potentially hot optical elements, such as LEDs 56, 61, from being touched while providing apertures of sufficient size so that they do not block the path of the illumination or the imaging path of the cameras.

While the contamination object classification 313 capabilities of the handheld inspection system can provide useful indications that contamination may be present, it cannot identify with high certainty the species or strain of specific pathogens. Other methods such as swabbing can be used in combination with laboratory analysis to accurately identify species or strain of specific pathogens. While these swabs can be very specific when analyzed, they do not necessarily contact areas where the contamination is present. According to some embodiments presently disclosed, the handheld system presently disclosed can be used to identify the areas of contamination. Once identified, before they are disinfected, they can be swabbed so that the species can be identified, providing additional information about the contamination. This provides significant cost, speed, and efficiency advantages over random swabbing methods.

According to some embodiments presently disclosed, the handheld system presently disclosed can be used to detect the presence of fluorescence tags or labels 311. These labels can be designed to bind to specific proteins and when bound to the proteins become fluorescent. In the absence of the protein, they do not fluoresce. The labels can be applied by spraying or misting onto a surface or applying them in some other way. The labels can also be integrated with a swab material or other substrate surface built into a tray or armrest, etc.

Antimicrobial coatings are increasingly being applied to high touch surfaces prone to cross contamination. By incorporating a fluorescent dye in these coatings, it is possible to detect when they become worn and ineffective as the fluorescence signal diminishes. According to some embodiments presently disclosed, a fluorescent dye suitable for detection by the CSI-D device is incorporated in the antimicrobial coating and the handheld system is used to monitor the status of antimicrobial coating and when it needs to be reapplied.

According to some embodiments presently disclosed, one of the cameras 25, 30 incorporates an image sensor that is sensitive to wavelength of light in the infrared region and detects temperature differences and patterns that reveal the existence of water/moisture. Moist surfaces are prone to encourage growth of bacteria, fungi, and mold.

According to some embodiments presently disclosed, a dynamic risk management method 1500 may be used to keeps track of the actual risk status of every location that requires sanitation. It adjusts risk level based on frequency of use, physical properties, proximity to contamination sources, sanitization history, and local risk profiles. It automatically adjusts inspection task lists to respond dynamically to real time risk conditions including incidents 1510.

According to some embodiments presently disclosed, an Artificial Intelligence (AI) risk management may transform risk strategy from reactive to proactive. The AI algorithm accepts initial risk 1540 and ongoing risk 1530 assessments from internal stakeholders to rate the likelihood and potential impact of risks for each location and surface type and adjusts risk profiles and inspection task list accordingly 1545. The AI algorithm may constantly learn 1520 when the presently disclosed system is used before and after cleaning procedure and automatically identifies spot vulnerabilities, bottlenecks, and compliance shortfalls.

Figure 15:
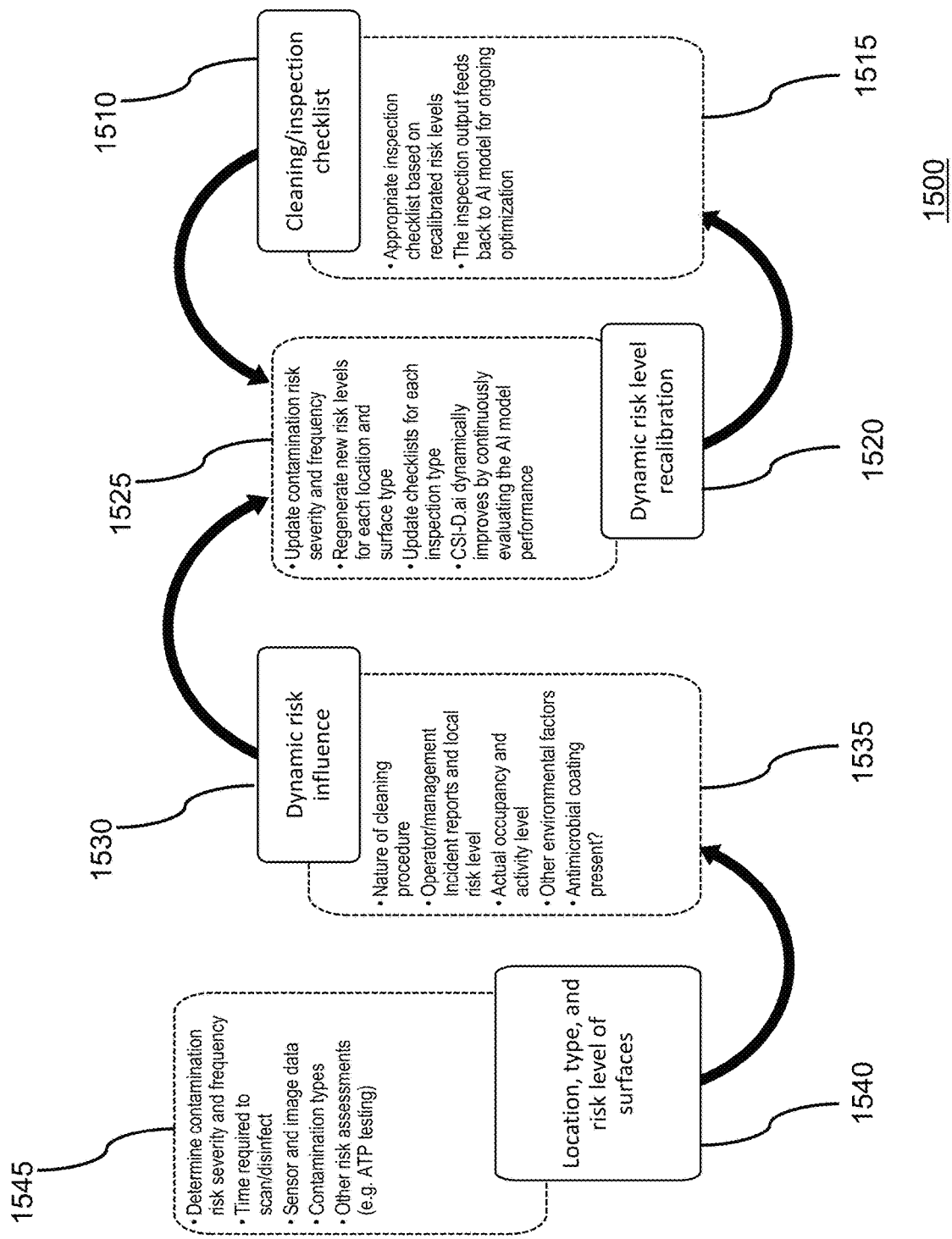
FIGS. 15-16 depict a block diagram of dynamic risk management algorithms according to some embodiments presently disclosed.

The AI system may constantly update weighted risk scores 1520, 1525 and lets users dig into reporting and analysis with custom analytics and heat maps that deliver in-depth, real-time data on critical risks across your enterprise. FIG. 15 depicts an exemplary Artificial intelligence algorithm for dynamic risk assessment according to some embodiments presently disclosed.

According to some embodiments presently disclosed, an automatic document collection with a workflow management system may be used to facilitate deadline-triggered requests, transparent tracking, and notifications. Easily generate mitigations from data gathered in risk assessments. Transform findings into action items assigned to individuals with deadlines and automated reminders. Automate continuous monitoring of new and existing risk activity for increased visibility.

Figure 16:
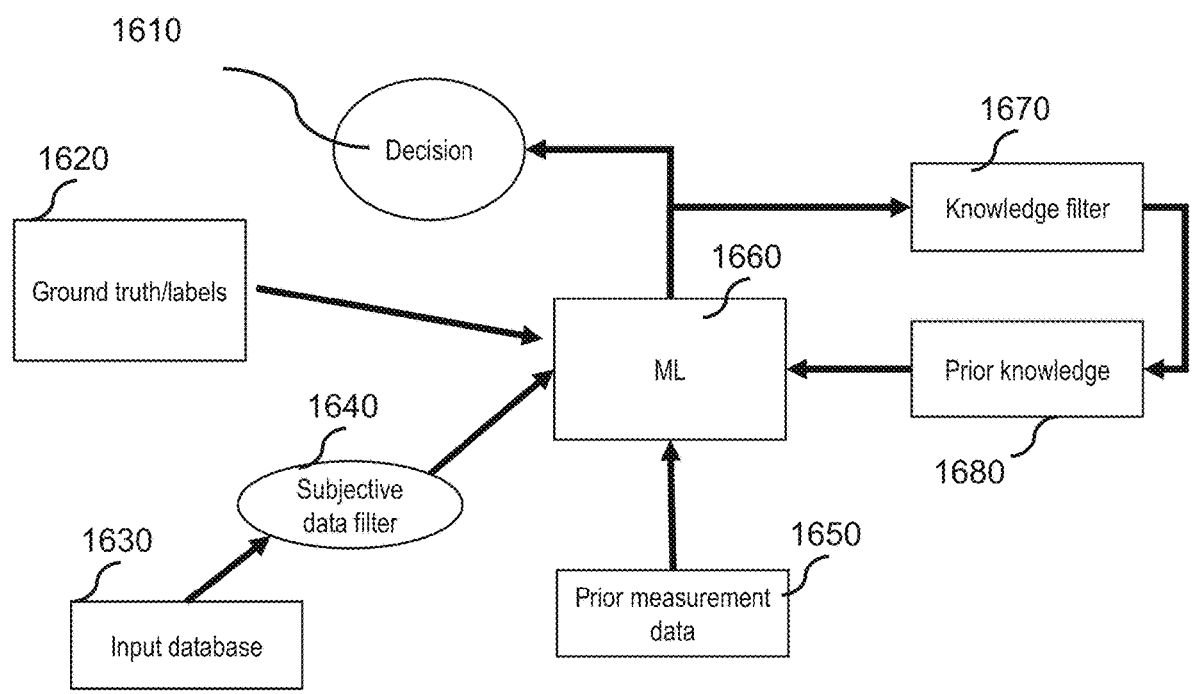

According to some embodiments presently disclosed, Artificial Intelligence (AI) algorithm may use a library of configurable process apps built specifically for governance, risk, and compliance controls and lets you further customize each process to match the unique demands of your organization. FIG. 16 depicts an exemplary artificial intelligent algorithm flowchart according to some embodiments presently disclosed. The machine learning algorithm accepts prior sensor data 1650 from CSI-D system, the input database 1630 including the location, risk index, material, and prior reference to risk index values reflected from multiple industry SSOPs in practice. The input database can be subjectively filtered 1640 based on the expert review and assigned groundtruth labels for the risk 1620. The ground truth/labels 1620 are the information from statistical data, or industry consensus assessment as an input to train the machine learning algorithm 1660. The ML can use prior measurement data from at least one measurement tool including at least one of CSI-D or swab-based measurements (e.g., ATP) for training the machine learning model. The purpose of machine learning model 1660 to provide risk assessment that can be used to prioritize inspection tasks. There is typically insufficient time for operators to inspect every potential site of contamination every day. Inspection tasks need to be prioritized based on risk. Risk constantly changes due to external factors such as local disease prevalence, increased frequency of use of or contact with, the location being inspected, and the time interval since the last inspection. All of these become inputs to the risk level for the location and impact the scheduling. Other factors that impact the risk is the history of the contamination identified each time a location is measured with the CSI-D and or other third-party measurement tools such as swabbing. The inspection tasks will change for any particular inspection job to accommodate the time available for inspection with the level of acceptable cleanliness risk for the location. Changes in frequency of contamination can be a result of the external factors described above or internal processes such as cleaning effectiveness of different cleaning staff or changes in the method of cleaning and monitoring of the dynamically change of risk can be used by the management to identify an improved sanitation process.

According to some embodiments presently disclosed, presently discloses system may provide incident management through a web portal or the device 10's user interface. Potential incidents may be logged, and a First Response may be initiated quickly and efficiently. The device server 90 and/or external server 95 may send an incident response checklist that guides the responder through the Detection & Analysis process. Presently disclosed system may automatically identify contaminants as the responder scans surfaces in the incident area. Upon detection of contamination, the responder may be prompted to trigger disinfection with intense UV light. The presently disclosed system may automatically control the amount of light delivered depending on the distance of the device 10 and the area to be disinfected. The surface can then be cleaned safely and re-scanned to verify that there is no trace of contamination left on the surface. The Disinfection & Verification process may be electronically documented for all detected contaminated surfaces until the checklist is complete. Post Incident Activity includes intuitive reports and dashboards that let management track how well the organization responds to incidents and ensures incidents are resolved within defined timeframes.

Figure 17:
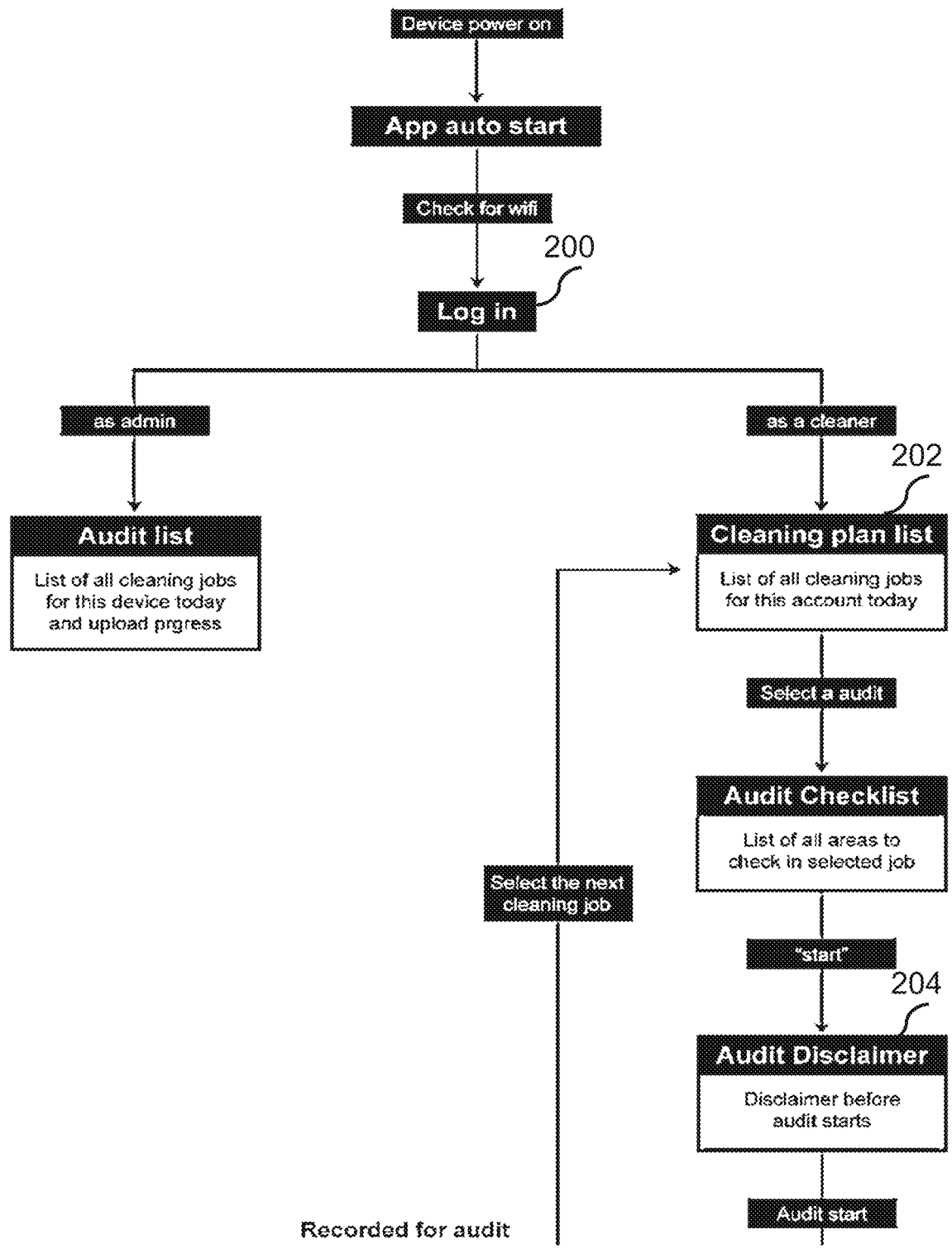
FIG. 17 depicts an exemplary audit initialization flowchart according to some embodiments presently disclosed.

FIG. 17 depicts an exemplary audit initialization flowchart according to some embodiments presently disclosed.

Figure 18:
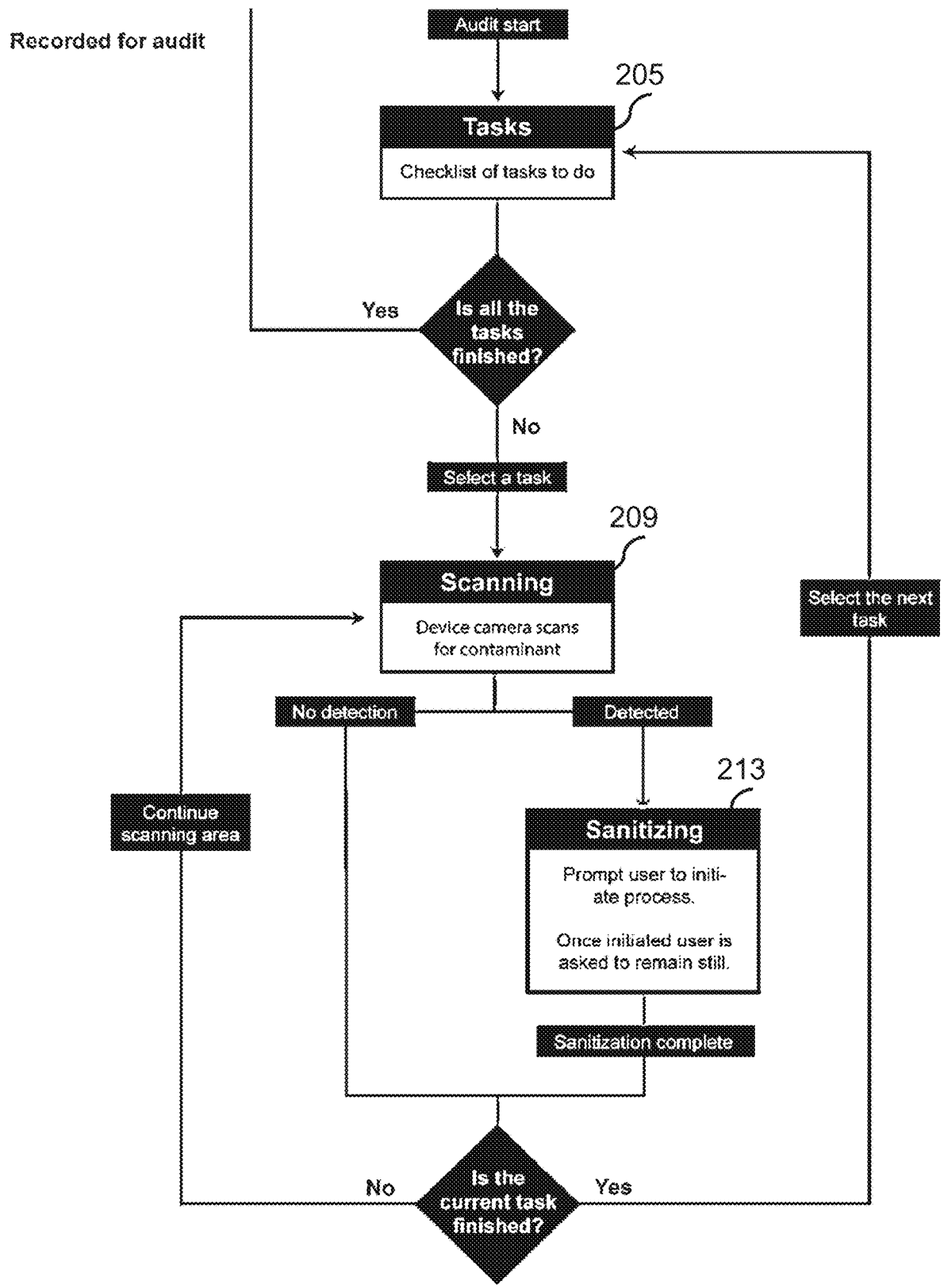
FIG. 18 depicts an exemplary audit task flowchart according to some embodiments presently disclosed.

FIG. 18 depicts an exemplary audit task flowchart according to some embodiments presently disclosed.

Figure 19A:
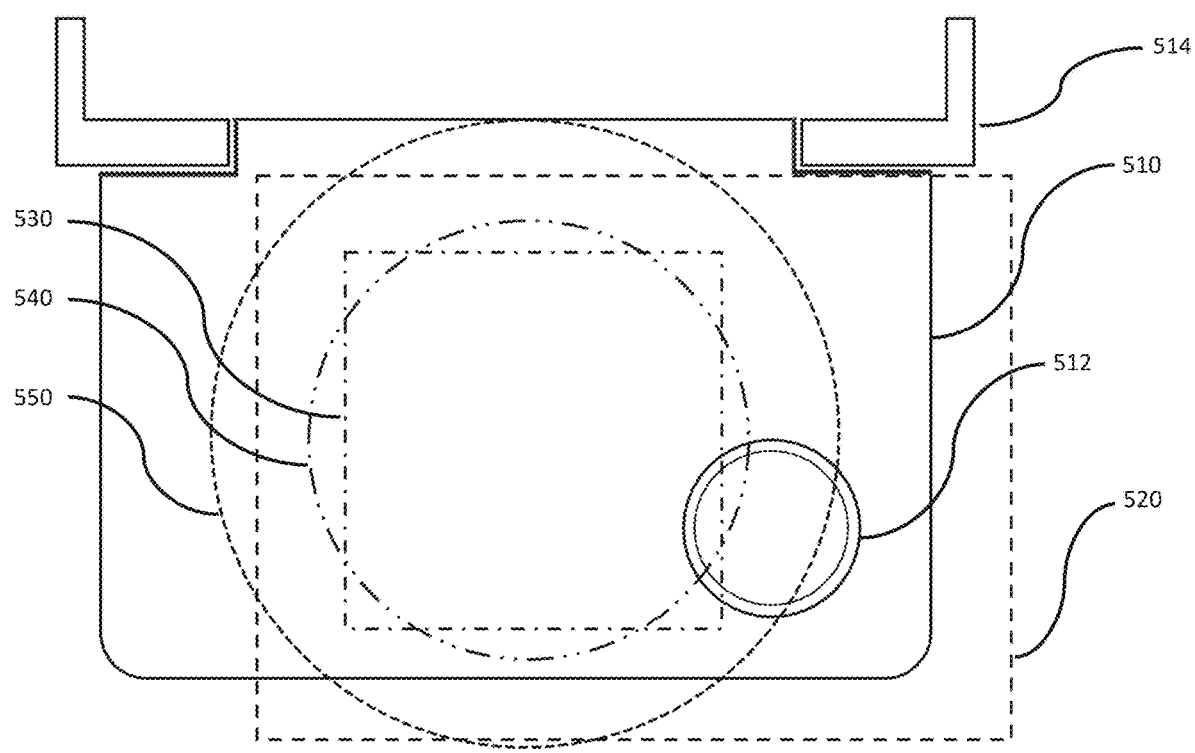
FIGS. 19a-q depict image fields of view according to some embodiments presently disclosed.
Figure 19B:
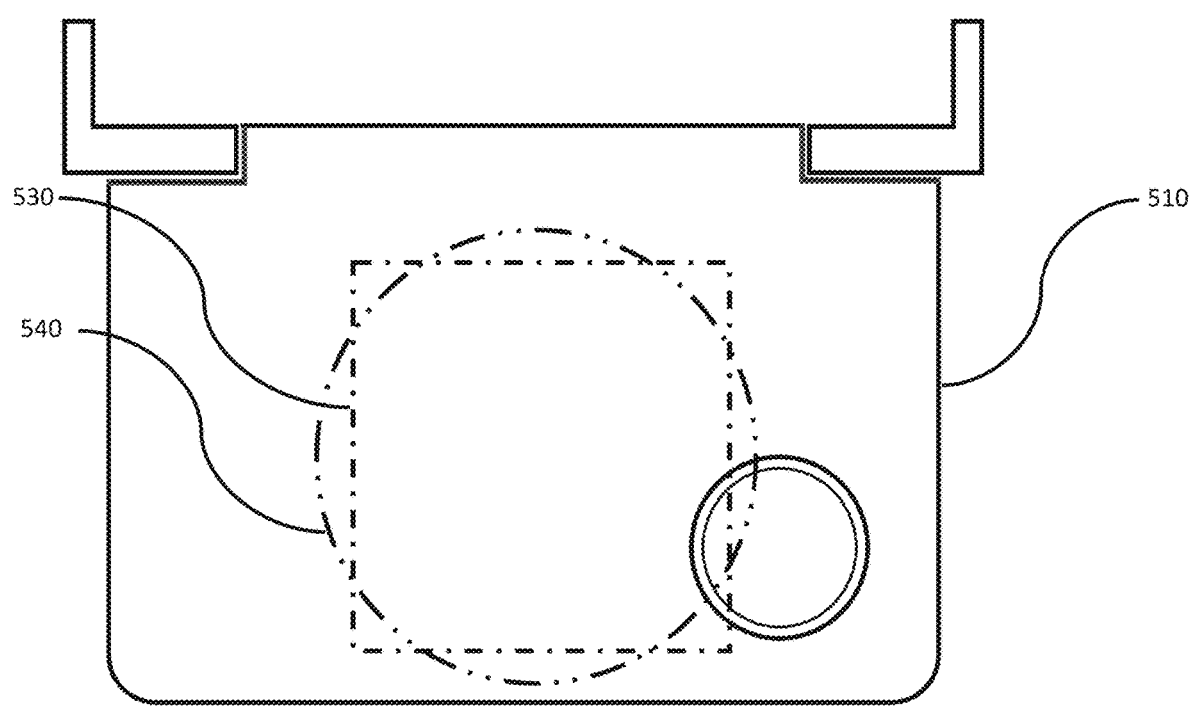

FIGS. 19a-b depict a line drawing of an image field of view during a sanitation inspection with the device 10 and showing the relative positions of the camera fields of view and the illumination areas according to some embodiments presently disclosed. The object being imaged is an example of an airline tray table 510 showing cupholder 512 and support brackets 514. Dashed line 520 shows the field of view of camera system 25 that can capture blue-violet fluorescence excitation images as well as background images under ambient light illumination. Dashed line 530 shows the field of view of camera system 30 that can capture UV fluorescence excitation images as well as background images under ambient light illumination. Dashed line 540 shows the field of illumination of the blue-violet fluorescence excitation light on the airline tray table 510. Dashed line 550 shows the field of illumination of the UV fluorescence excitation light on the airline tray table 510.

Figure 19C:
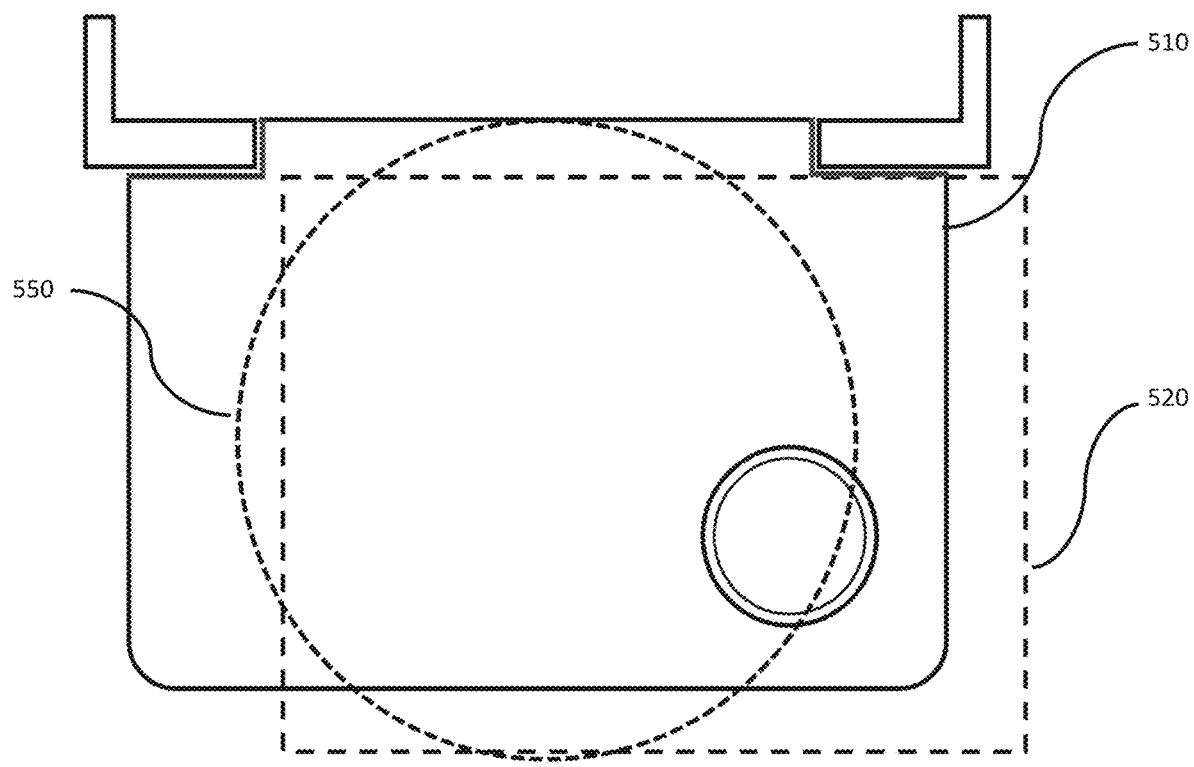

FIG. 19c depicts a line drawing showing airline tray table 510 and just the image field of view for camera system 25 that can capture blue-violet fluorescence excitation images. Dashed line 520 shows the field of view of camera system 30 that can capture blue-violet fluorescence excitation images as well as background images under ambient light illumination. Dashed line 550 shows the field of illumination of the blue-violet fluorescence excitation light on the airline tray table 510.

Figure 19D:
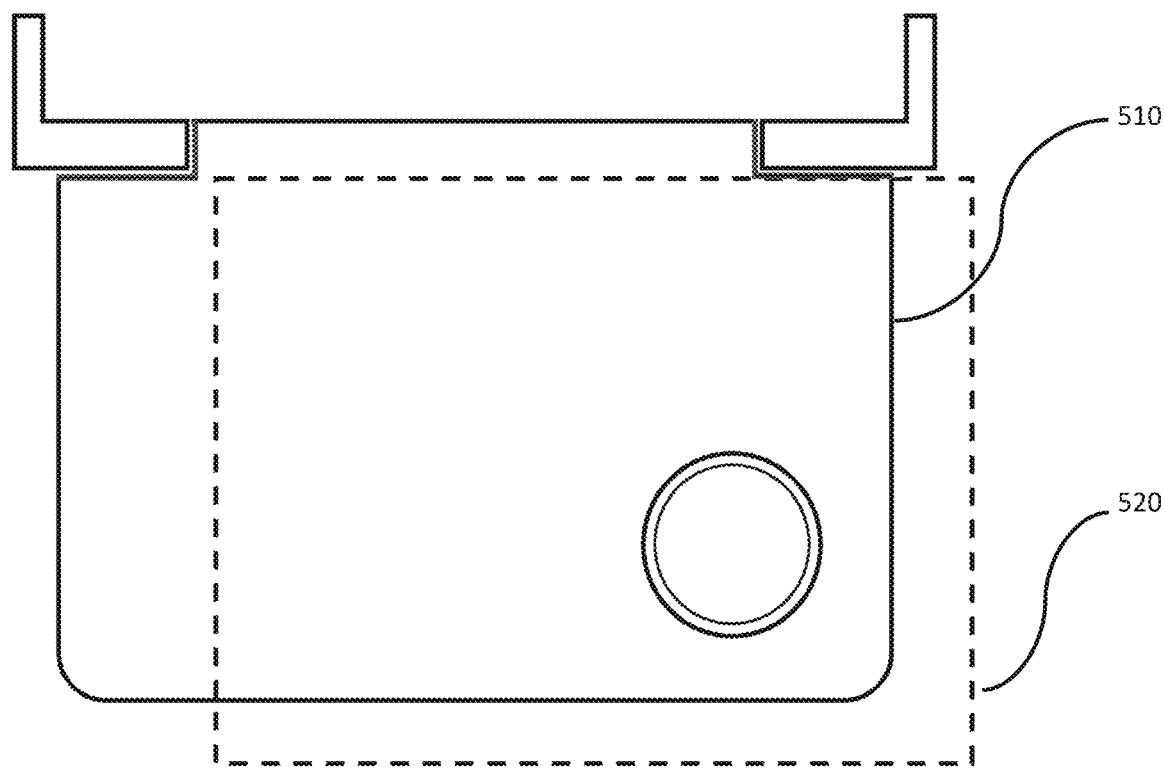

FIG. 19d depicts a line drawing showing airline tray table 510 and just the image field of view for camera system 25 that can capture blue-violet fluorescence excitation images. Dashed line 520 shows the field of view when camera system 30 captures only a background image under ambient light illumination.

Figure 19E:
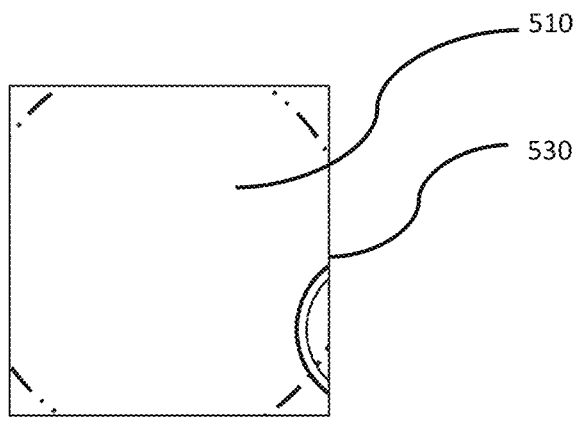

FIG. 19e depicts a line drawing representing a square image of a portion of tray table 510 captured by camera system 25 that can capture UV fluorescence excitation images.

Figure 19F:
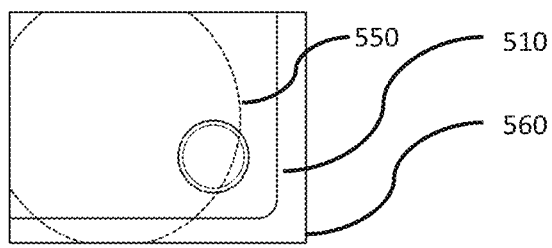

FIG. 19f depicts a line drawing representing a 4:3 aspect ratio image 560 of a portion of tray table 510 with a larger field of view, but fewer pixels, than the square image in FIG. 19e, and captured by camera system 25 that can capture blue violet fluorescence excitation images with a filter combination 26, 27 that selects red-infrared wavelength regions.

Figure 19G:
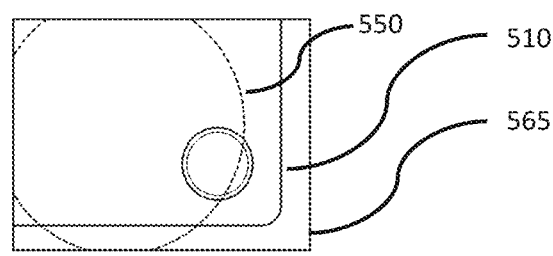

FIG. 19g depicts a line drawing representing a 4:3 aspect ratio image 565 of a portion of tray table 510 with a larger field of view, but fewer pixels, than the square image in FIG. 19e, and captured by camera system 25 that can capture blue violet fluorescence excitation images with filter combination 26, 27 that selects green wavelength regions.

FIGS. 19h-j depict a line drawing representing a 4:3 aspect ratio red image 570, green image 575, and blue image 580 of a portion of tray table 510 with a larger field of view, but fewer pixels, than the square image in FIG. 19e, and captured by camera system 25 that can capture blue-violet fluorescence excitation images, but with no excitation illumination and capturing only reflectance images under ambient light illumination.

FIGS. 19k-l depict a line drawing representing UV fluorescence excitation image 530, which is then scaled so that it matches the scale, in terms of number of pixels to size of real-world objects of at least one of image 560, image 565, image 570, image 575 and image 580.

FIGS. 19m-n depict a line drawing representing blue-violet fluorescence excitation image 560 and image 565 and showing the corresponding size and relative location 585 in the field of view of scaled image 535 to which image 560 and image 565 are to be cropped so the images can be registered for further image processing and analysis.

Figure 19O:
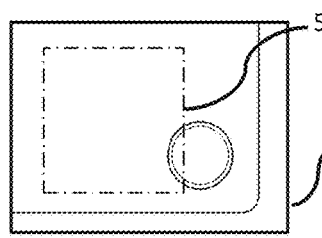
Figure 19P:
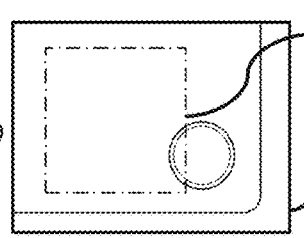
Figure 19Q:
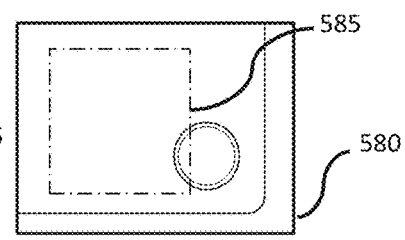

FIGS. 19o-q depict a line drawing red image 570, green image 575, and blue image 580 and showing the corresponding size and relative location 585 in the field of view of scaled image 535 to which image 570, image 575, and image 580 are to be cropped so the images can be registered for further image processing and analysis.

Referring to FIGS. 20-35, user's interactions with the device 10 is shown according to some embodiments presently disclosed.

Figure 20:
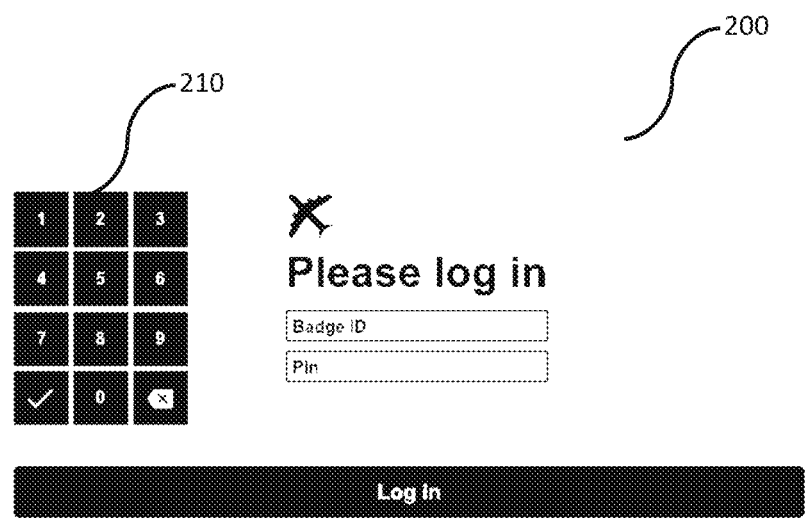
FIGS. 20-35 depict user interface according to some embodiments presently disclosed.

According to some embodiments presently disclosed, in response to a series of gestures (e.g. finger taps) by the user, the screen 70 displays a log in screen 200 with one or more icons (i.e. virtual buttons) 210 (shown in FIG. 20). According to some embodiments presently disclosed, in response to activation of the one or more hand controls 80 by the user, the screen 70 displays a log in screen 200 with one or more icons (i.e. virtual buttons) 210 (shown in FIG. 20) on the display 70. Information may be displayed in a portrait view (shown in FIG. 20) or a landscape view (not shown) based on an analysis of data received from the one or more accelerometers 168.

Figure 21:
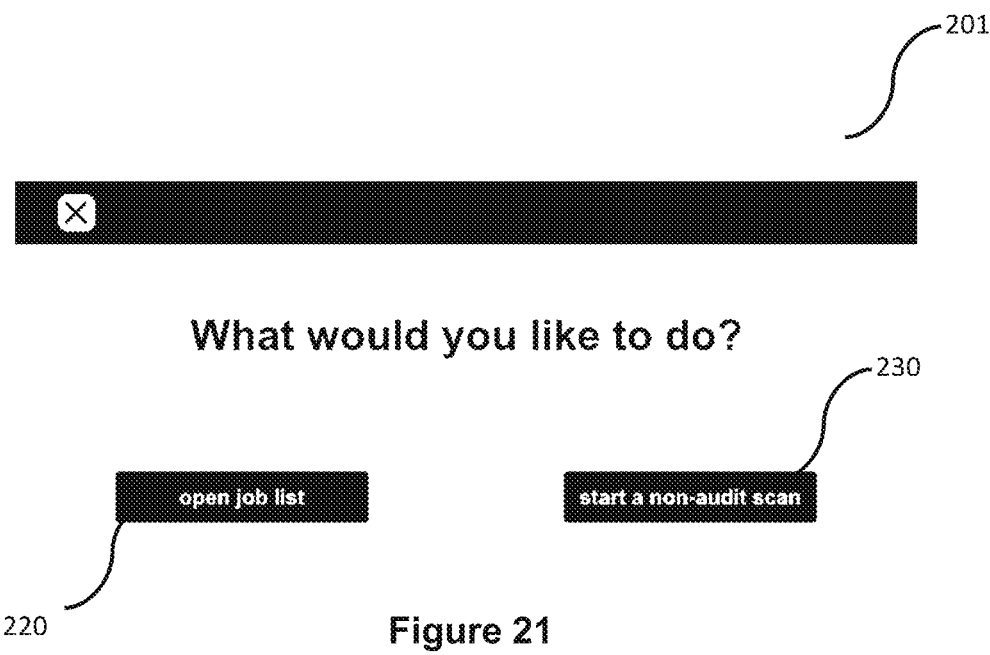
Figure 22:
Figure 23:
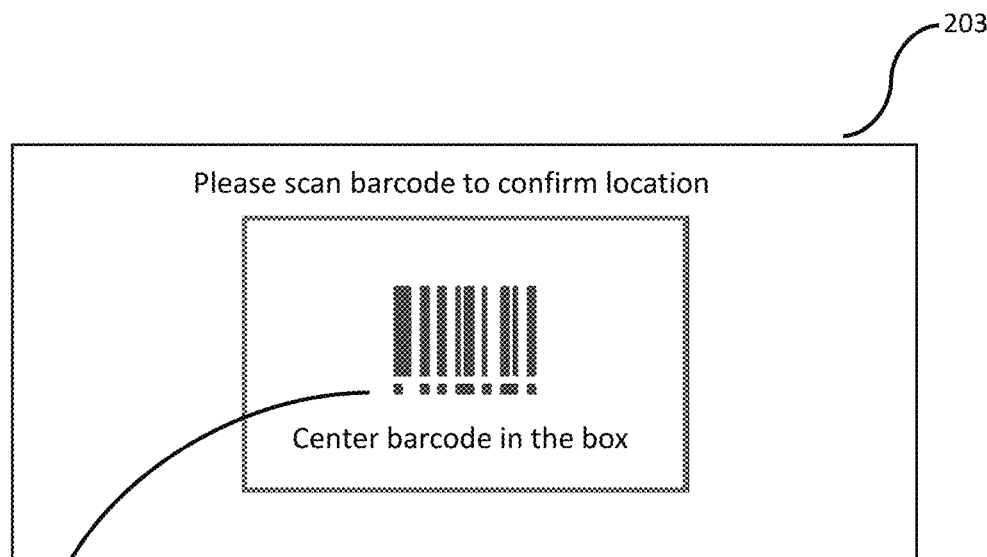
Figure 24:
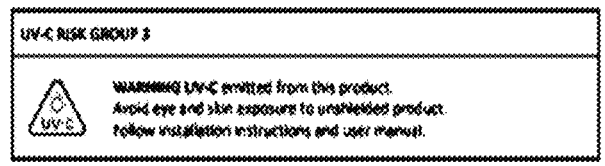
Figure 24:
Figure 24:
Figure 24:
Figure 25:
Figure 26:
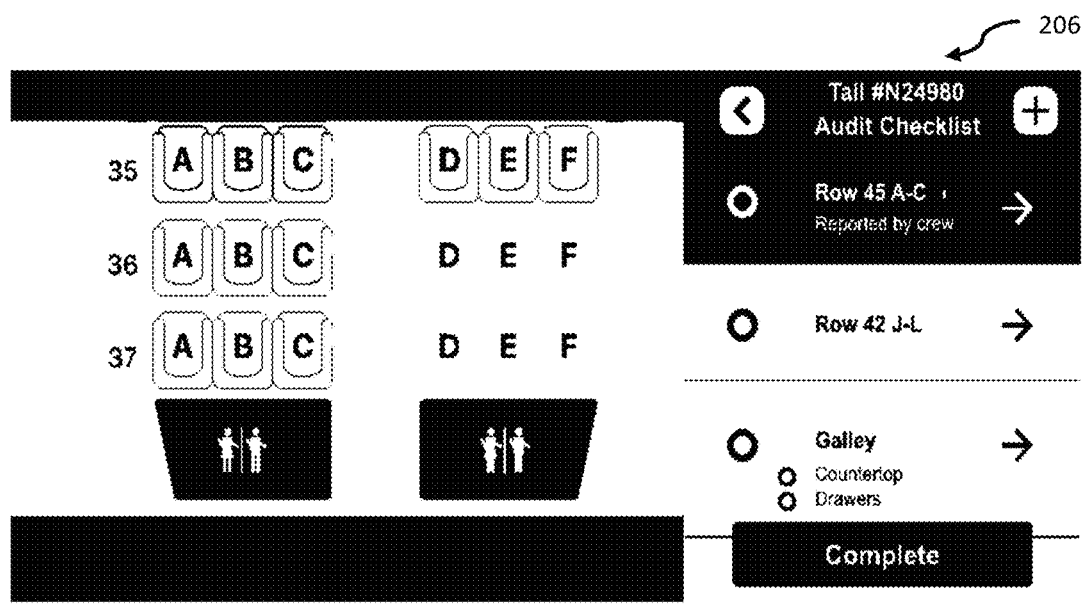

According to some embodiments, after entering correct log in information, the screen 70 displays screen 201 with one or more icons 220, 230 (shown in FIG. 21). According to some embodiments, in response to detecting a finger contact with the icon 220 on the screen 70, the device 10 displays screen 202. According to some embodiments, the screen 70 displays screen 202 with one or more icons 240, 250, 260 (shown in FIG. 22). The one or more icons 240, 250, 260 may represent one or more jobs from a job list.

According to some embodiments, in response to detecting a finger contact with the icon 240 on the screen 70, the device 10 displays screen 203. According to some embodiments, the device 10 turns on one of the cameras 25, 30 to allow the user to take a picture of a barcode 241 located in an area associated with the job selected from the screen 202 (shown in FIG. 23). According to some embodiments, activating the camera 25 or 30 takes a picture of the barcode and compares it to a barcode associated with the area associated with the job 240 selected from the screen 202. If the barcode 241 does not match the barcode associated with the job 240, the device 10 displays screen 203 to allow the user to try again.

According to some embodiments, if the barcode 241 matches the barcode associated with the job 240, the device 10 displays screen 204 to allow the user to confirm the correct area and that the user acknowledges all safety measures have been considered by activating icon 270. According to some embodiments, if the barcode 241 matches the barcode associated with the job 240, the device 10 displays screen 204 to remind the user of safety measures before proceeding further. The safety measures may be eye protection, gloves, distance from other people. According to some embodiments, once the user is ready to inspect the area, the user activates an icon 280 on the screen 205 (shown in FIG. 25) and is taken to the task list screen 206. Task list screen 206 displays all tasks related to the job in a sequential order.

Figure 36:
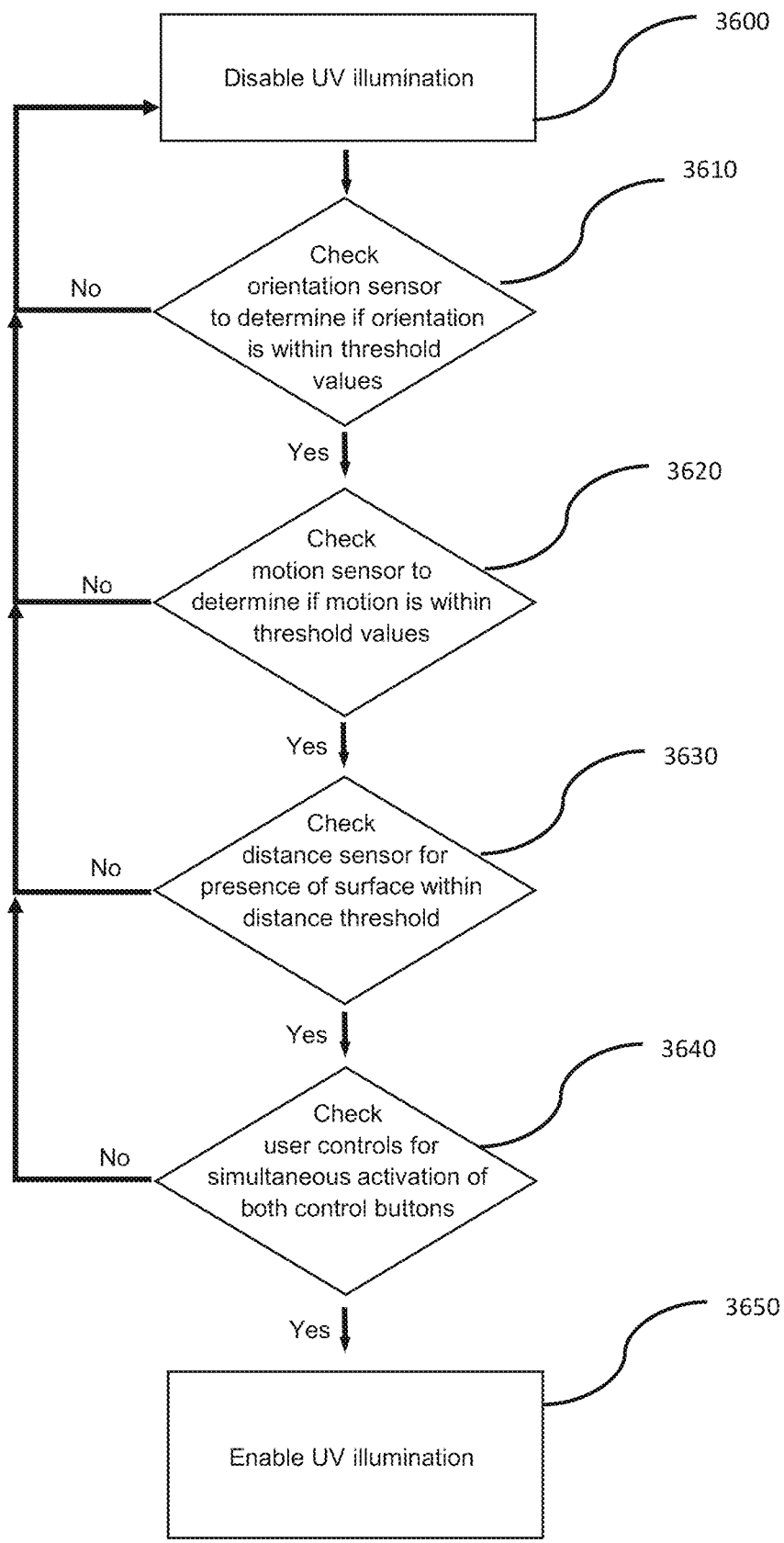
FIG. 36 depicts a system software safety algorithm according to some embodiments presently disclosed.

According to some embodiments, before starting the scan, device 10 performs safety checks as described in FIG. 36.

Figure 27:
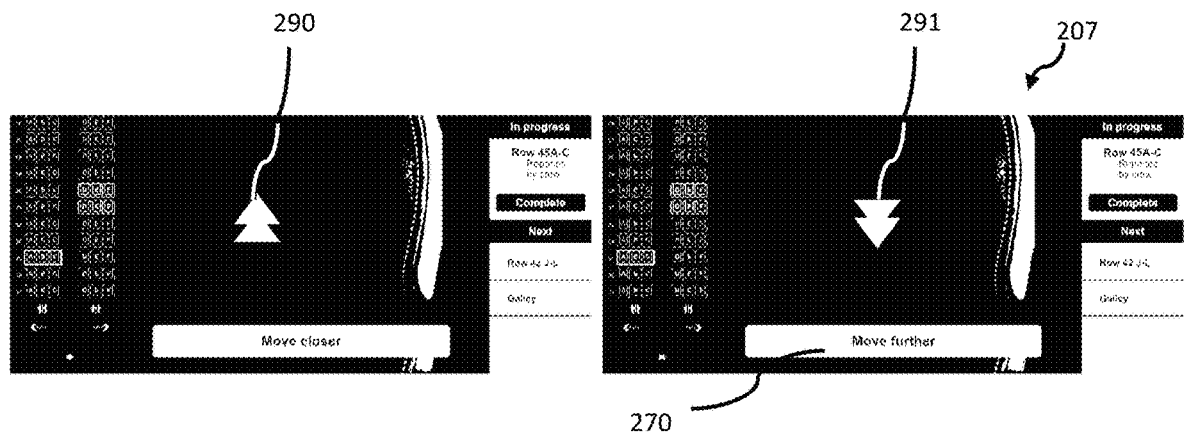

According to some embodiments, one the inspection begins, device 10 guides the user with one or more icons 290, 291 shown in screen 207 (FIG. 27). The icon 290 may instruct the user to move the device 10 closer to a surface being inspected. The icon 291 may instruct the user to move the device 10 further away from a surface being inspected.

Figure 28:
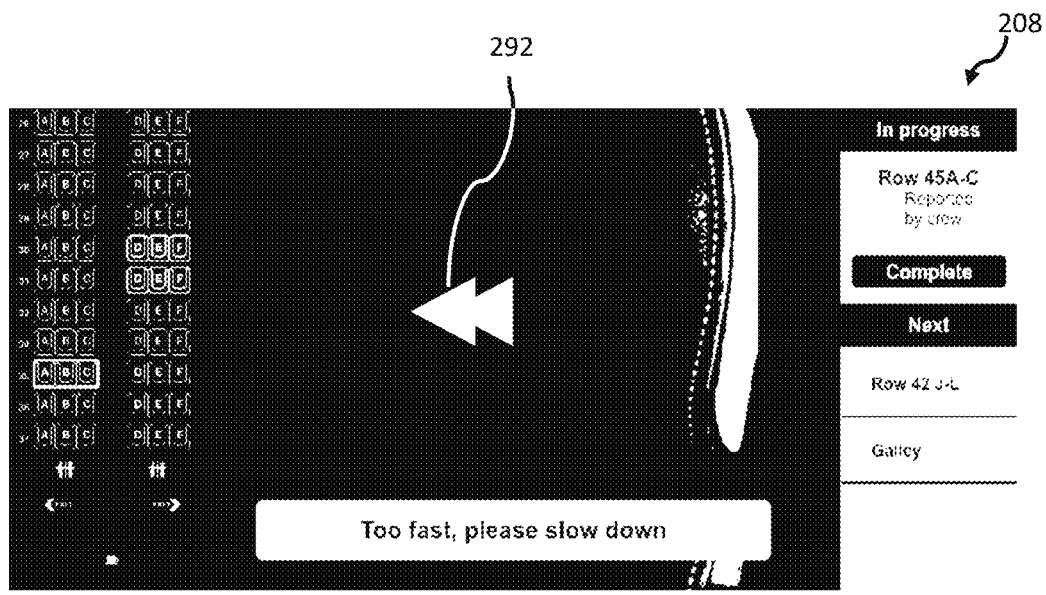
Figure 29:
Figure 30:
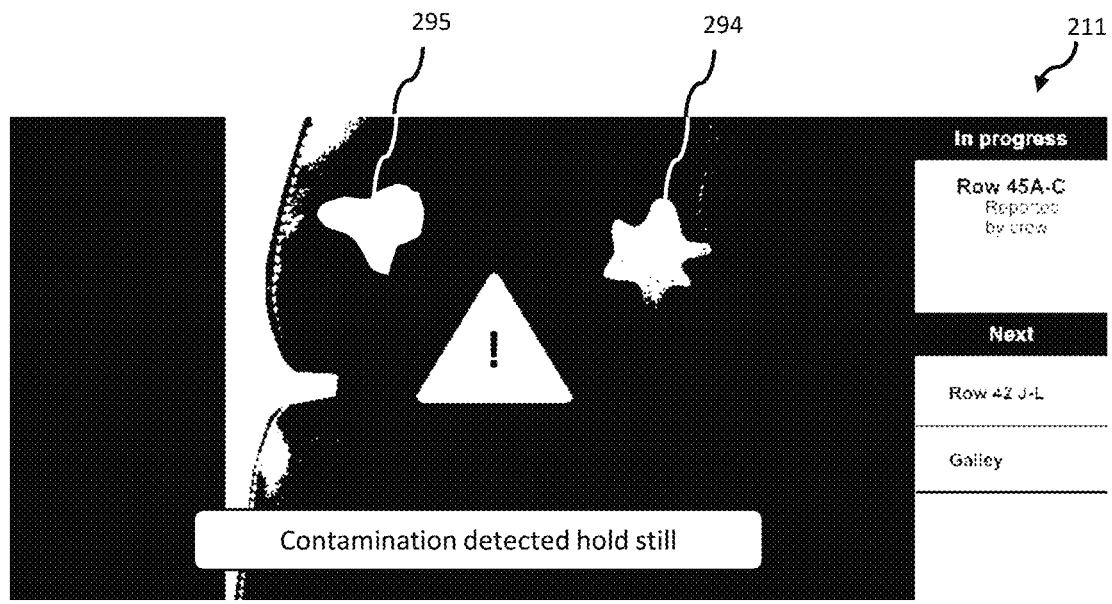
Figure 31:
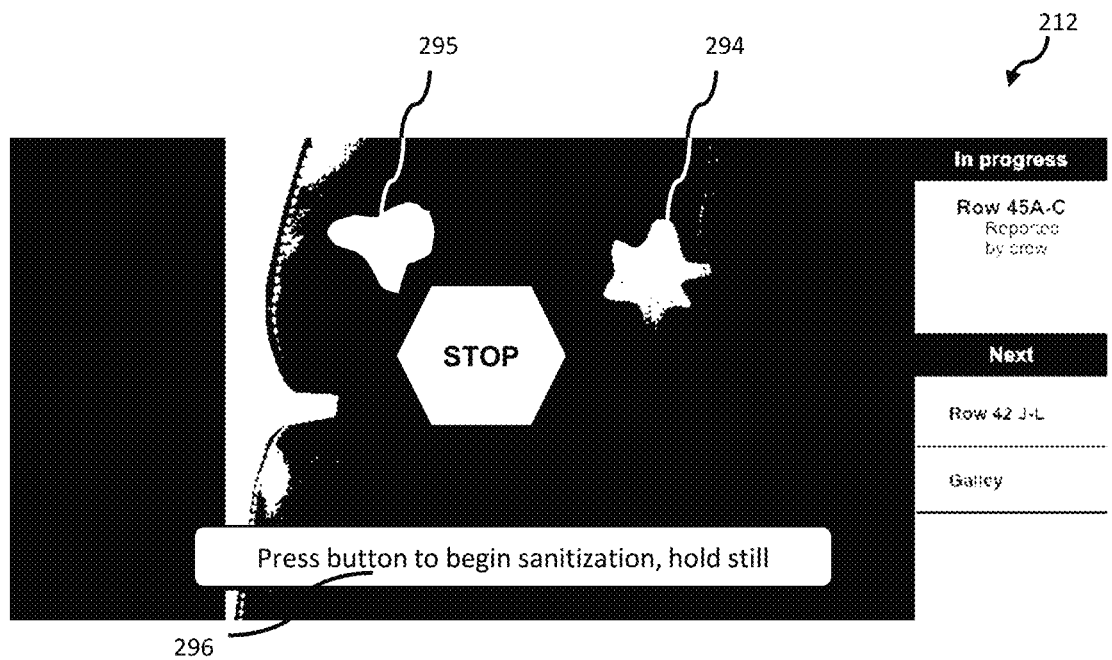

According to some embodiments, one the inspection begins, device 10 guides the user with one or more icons 292, 293 shown in screens 208, 208 (FIGS. 28-29). The icons 292, 293 may instruct the user to move the device 10 slower across a surface being inspected.

According to some embodiments, during the inspection the device 10 processes one or two video sources with background subtraction and image registration combined with a single stream. The device 10 may further analyze fluorescence images for presence of contamination. If contamination is detected, device 10 displays screen 211 showing contaminants 294, 295. According to some embodiments, the contaminants are not visible to the user and device 10 overlays a computer generated image over the portion of the surface where contaminants were detected. These computer generated images are shown as icons 294, 295.

According to some embodiments, if contaminants are detected, device 10 may prompt the user to start disinfection of the contaminated surface by displaying screen with icon 296. According to some embodiments, the device 10 uses distance sensor 50 to measure distance to the surface to be disinfected and calculates exposure required for disinfection.

The disinfection time is dependent on the species to be disinfected or deactivated, different species different amount of UV energy at a particular wavelength to produce disinfection effects. FIG. 14 shows an example of UVC energy (mJ/cm$^2$) required to kill *Streptococcus pneumoniae* serotype 6A bacteria. The disinfection can be partial or virtually complete as described above when discussing "Log reduction". The greater "Log reduction" desired the more energy needs to be delivered as shown in FIG. 14. Once the energy requirement is determined and the distance to the surface was determined the system can calculate from the previously known/calibrated energy distribution at various distances, the amount of time required to deliver the energy required for a desired species to be disinfected. Determination of energy requirement can also be varied by the size or thickness of the contamination or whether it is dry, in solution, or present in a biofilm, fecal matter, or food contamination. The thickness and material containing the contamination can absorb the disinfecting UV light and reduce the effectiveness. By determining the size, thickness or concentration of the contamination material that may contain a pathogen the system can modify the time required so that sufficient energy is delivered to disinfect (kill or deactivate) the pathogen. The system can determine the size, thickness, and concentration by image analysis of the fluorescence image acquired by camera 25 and 30.

Figure 32:
Figure 33:
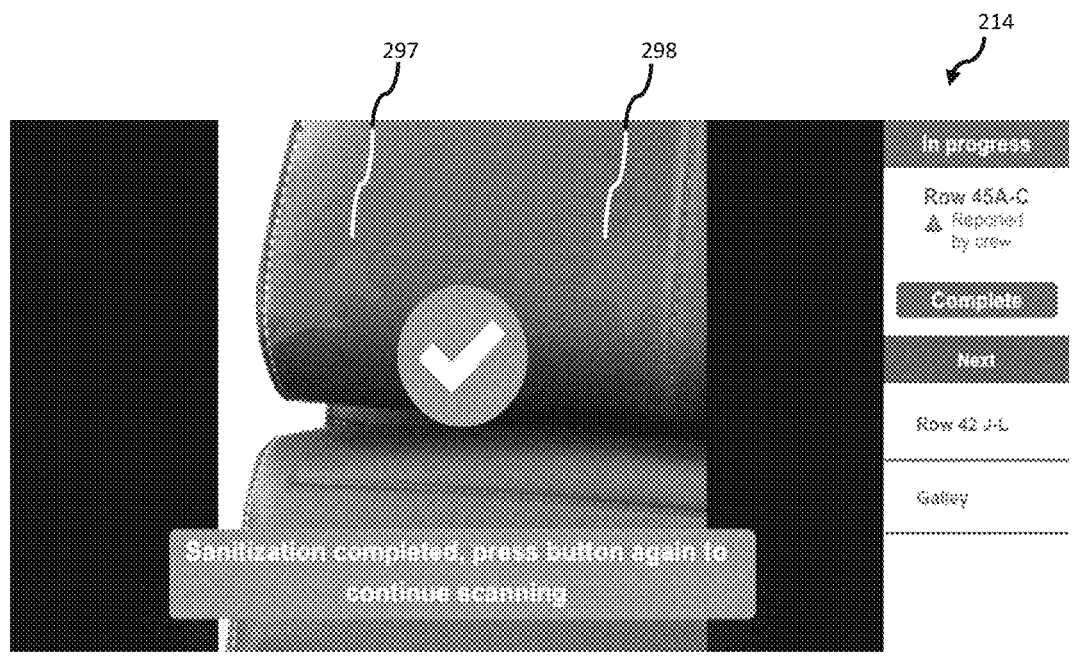
Figure 34:
Figure 35:
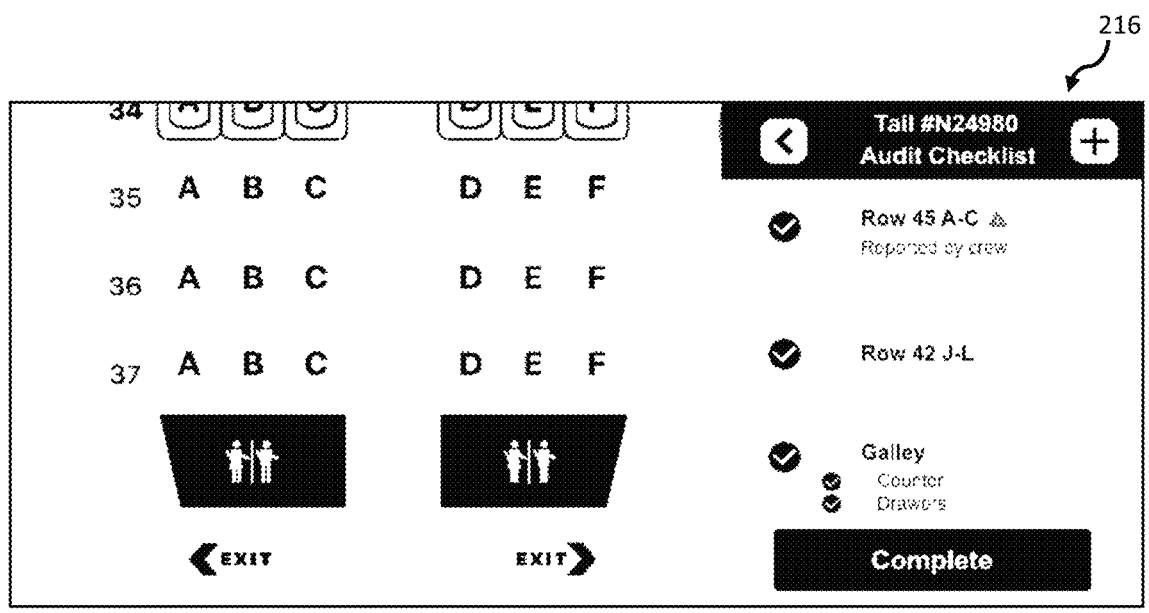

According to some embodiments, device 10 displays screen 213 while disinfection is in progress (shown in FIG. 32). According to some embodiments, device 10 displays screen 214 when the disinfection is completed (shown in FIG. 33). The screen 214 may depict computer generated images 297, 298 to represent areas that were contaminated. The computer images 297, 298 are displayed in a different color from the computer generated images 294, 295. For example, computer generated images 294, 295 may be displayed in red color to signify contamination and computer generated images 297, 298 may be displayed in green color to signify those areas being disinfected and free from contamination.

According to some embodiments, the device 10 records one or more videos during the inspection and/or disinfection process. The one or more videos may be stored in the memory 74 and/or in the memory of the device server 90.

According to some embodiments, the device 10 displays screen 215 once disinfection is complete. According to some embodiments, the device 10 displays screen 202 to allow the user to start scanning another area by selecting icons 250 or 260. After selecting 250 or 260, device 10 displays 216 (shown in FIG. 35).

According to some embodiments, at the end of the audit, device 10 may show all tasks are check marked and an audit report for the entire aircraft with contaminations found, disinfections, videos etc. will be stored for upload to the cloud database.

According to some embodiments, safety checks are preformed continuously throughout scan process and disinfection process.

According to some embodiments, the operator may select toggle view button to start looking for saliva residue contaminants (LED:270 nm, UV camera). the device 10 may display the 270 nm fluorescence image on the screen. The camera will be in free run mode at 10 fps. The algorithm checks for hot spots and records the frame numbers and alerts the app. The fluorescence imaging mode will automatically switch back to default mode after 10 seconds. The app needs to notify the user when it switches to the default mode (LED:405 nm, RGB camera).

According to some embodiments, the device 10, lighting sources 55, 60 and/or cameras 25, 20 may overheat. In case of overheating, the device 10 will disable scanning for a predetermined amount of time (for example 60 seconds) or until temperature goes down. When temperature is within working range after overheating event has happened, devoice 10 notifies the user to resume scanning.

According to some embodiments, the device 10 monitors power level and if level is below a predetermined threshold (for example 20% of the full battery) device 10 will determine and notify the user "X minutes of scanning left".

According to some embodiments, the device 10 determines if human is in the view of RGB camera. The device 10 disables inspection/disinfection process if human is detected.

According to some embodiments, if user presses "shutdown" button on the device 10, the device 10 will send "shutdown" event and may record shutdown event as a part of an audit if audit is in progress.

According to some embodiments, the device 10 monitors accelerometer and reports changes in acceleration that can be harmful for the device 10. Such events may be stored in the log for further uploading to the cloud. Such events may be reported as a part of an audit if it occurs during the audit.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software-based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ".

What is claimed is:

1. A device comprising:
    a first light source configured to excite fluorescence emission of a first contaminant on a surface;
    a first optical sensor configured to capture one or more images of the fluorescence emission of the first contaminant; and
    a display configured to depict the surface and a first computer generated image representing the contaminant, wherein the first computer generated image covers at least a portion of the surface shown on the display;
    wherein the first contaminant comprises at least one pathogen;
    wherein the first light source comprises illumination of suitable wavelengths and power to kill the at least one pathogen;
    wherein the first computer generated image comprises a first color: wherein the display is configured to depict the first computer generated image comprising a second color,
    wherein the first computer generated image comprising the second color covers at least the portion of the surface shown on the display after the at least one pathogen is killed.

2. The device of claim 1, wherein the first light source comprises illumination of suitable wavelengths and power to deactivate the first contaminant.

3. The device of claim 1, wherein the first light source provides illumination light in an ultraviolet (UV) wavelength range between 260 nm and 290 nm.

4. The device of claim 1, wherein the first optical sensor is configured to capture at least one image of the fluorescence emission in an ultraviolet (UV) wavelength range between 320 nm and 370 nm.

5. The device of claim 1, wherein the first optical sensor is configured to capture at least one images of the fluorescence emission in a first wavelength band.

6. The device of claim 5, wherein the first wavelength band is ultraviolet (UV) band.

7. The device of claim 5, wherein the first wavelength band is visible band.

8. The device of claim 5, further comprises a second optical sensor configured to capture one or more images of the fluorescence emission of the first contaminant.

9. The device of claim 8, wherein the second optical sensor is configured to capture one or more images of the fluorescence emission in a second wavelength band.

10. The device of claim 9, wherein the second wavelength band is ultraviolet (UV) band.

11. The device of claim 9, wherein the second wavelength band is visible band.

12. The device of claim 1 further comprises a second light source configured to excite fluorescence emission of the first contaminant on the surface.

13. The device of claim 12, wherein the second light source is a second plurality of light-emitting diodes (LEDs).

14. The device of claim 1, wherein the first light source is a first plurality of light-emitting diodes (LEDs).

15. The device of claim 1 further comprises:
    a second light source configured to excite fluorescence emission of the first contaminant on the surface; and
    a second optical sensor configured to capture one or more images of the fluorescence emission of the first contaminant;
    wherein the first light source provides illumination light in a first wavelength range;
    wherein the second light source provides illumination light in a second wavelength range;
    wherein the first optical sensor is configured to capture at least one images of the fluorescence emission in a first wavelength band;
    wherein the second optical sensor is configured to capture at least one images of the fluorescence emission in a second wavelength band.

16. The device of claim 15, wherein the first light source comprises illumination of suitable wavelengths and power to deactivate the first contaminant.

\* \* \* \* \*